(12) United States Patent  
Smith et al.

(10) Patent No.: US 10,166,533 B2  
(45) Date of Patent: Jan. 1, 2019

(54) METHODS FOR PRODUCING BORYLATED ARENES

(71) Applicants: Dow AgroSciences LLC, Indianapolis, IN (US); Board of Trustees of Michigan State University, East Lansing, MI (US)

(72) Inventors: Milton R. Smith, East Lansing, MI (US); Robert E. Maleczka, DeWitt, MI (US); Dmitrijs Sabasovs, Lansing, MI (US); Jossian Oppenheimer, Midland, MI (US)

(73) Assignees: Dow AgroSciences LLC, Indianapolis, IN (US); The Board of Regents of the University of Michigan, Ann Arbor, MI (US)

(*) Notice: Subject to any disclaimer, the term of this patent is extended or adjusted under 35 U.S.C. 154(b) by 255 days.

(21) Appl. No.: 14/740,814

(22) Filed: Jun. 16, 2015

(65) Prior Publication Data

US 2015/0361109 A1 Dec. 17, 2015

Related U.S. Application Data

(60) Provisional application No. 62/012,681, filed on Jun. 16, 2014.

(51) Int. Cl.
*B01J 31/22* (2006.01)
*C07F 5/02* (2006.01)
*B01J 31/18* (2006.01)

(52) U.S. Cl.
CPC ........... *B01J 31/22* (2013.01); *B01J 31/2295* (2013.01); *C07F 5/025* (2013.01); *B01J 31/181* (2013.01); *B01J 31/1815* (2013.01); *B01J 31/2273* (2013.01); *B01J 2231/4205* (2013.01); *B01J 2531/0216* (2013.01); *B01J 2531/845* (2013.01)

(58) Field of Classification Search
CPC .... B01J 31/22; B01J 31/2295; B01J 31/2273; B01J 31/181; B01J 31/1815; C07F 5/025
See application file for complete search history.

(56) References Cited

U.S. PATENT DOCUMENTS

| | | |
|---|---|---|
| 6,867,302 B2 | 3/2005 | Smith et al. |
| 6,878,830 B2 | 4/2005 | Smith et al. |
| 6,969,716 B2 | 11/2005 | Blackaby et al. |
| 7,314,849 B2 | 1/2008 | Balko et al. |
| 7,514,563 B2 | 4/2009 | Smith et al. |
| 7,611,647 B2 | 11/2009 | Arndt et al. |
| 7,915,200 B2 | 3/2011 | Epp et al. |
| 8,426,591 B2 | 4/2013 | Guenthenspberger et al. |
| 2003/0109713 A1 | 6/2003 | Smith et al. |
| 2006/0281939 A1 | 12/2006 | Smith et al. |
| 2009/0088322 A1 | 4/2009 | Epp et al. |
| 2010/0292227 A1 | 11/2010 | Yoakim et al. |
| 2011/0086759 A1 | 4/2011 | Aspinall et al. |
| 2012/0040936 A1 | 2/2012 | Kanno et al. |
| 2012/0115724 A1 | 5/2012 | Whittingham et al. |
| 2012/0190549 A1 | 7/2012 | Eckelbarger et al. |
| 2012/0190551 A1 | 7/2012 | Yerkes et al. |
| 2013/0005574 A1 | 1/2013 | Epp et al. |
| 2013/0172566 A1 | 7/2013 | Oppenheimer et al. |
| 2013/0172567 A1 | 7/2013 | Oppenheimer et al. |

FOREIGN PATENT DOCUMENTS

| | | |
|---|---|---|
| GB | 2484982 A | 5/2012 |
| WO | 2001064689 A1 | 9/2001 |
| WO | 2007082098 A2 | 7/2007 |
| WO | 2009023438 A1 | 2/2009 |
| WO | 2009029735 A1 | 3/2009 |
| WO | 2009081112 A2 | 7/2009 |
| WO | 2010125332 A1 | 11/2010 |
| WO | 2010149956 A1 | 12/2010 |
| WO | 2011073845 A1 | 6/2011 |
| WO | 2011075613 A1 | 6/2011 |
| WO | 2011103546 A1 | 8/2011 |
| WO | 2012033735 A1 | 3/2012 |
| WO | 2010116915 A1 | 10/2012 |
| WO | 2013003740 A1 | 1/2013 |
| WO | 2013016557 A2 | 1/2013 |
| WO | 2013101665 A1 | 7/2013 |
| WO | 2015077344 | 5/2015 |
| WO | 2015089119 | 6/2015 |
| WO | 2015149072 | 10/2015 |

OTHER PUBLICATIONS

Atienza et al. *Angewandte Chemie Int. Ed.* 2011, 50, 8143-8147.
Boller et al. *J. Am. Chem. Soc.* 2005, 127, 14263-14278.
Campos K. *Chemical Society Reviews* 2007, 36, 1069-1084.
Cheng et al. *Chemical Communications* 2012, 48, 8440-8442.
Cho et al. *J. Am. Chem. Soc.* 2000, 122, 12868-12869.
Cho et al. *Science* 2002, 295, 305-308.
Chotana et al. *J. Am. Chem. Soc.* 2005, 126, 10539-10544.
Chotana et al. *Tetrahedron* 2008, 64, 6103-6114.
Chotanta et al. *Chemical Communications* 2009, 38, 5731-5733.
Frieman, et al., *Synthesis* 2005, 17, 2989-2993.
Gilman et al. *J. Am. Chem. Soc.* 1939, 61, 109-112.
Hung-Low et al. *Chemical Communications* 2012, 48, 368-370.
Hung-Low et al. *Dalton Transactions* 2012, 41, 8190-8197.
International Search Report and Written Opinion dated Dec. 22, 2014 in International Application No. PCT/US2014/054366.
International Search Report and Written Opinion dated Sep. 2, 2015 in International Application No. PCT/US2015/07136054.
Ishiyama et al. *Angewandte Chemie Int. Ed.* 2002, 41, 3056-3058.
Ishiyama et al. *J. Am. Chem. Soc.* 2002, 124, 390-391.
Ishiyama T et al. *Chemical Communications* 2010, 46, 159-161.
Ito et al. *Organometallics* 2012, 31, 4442-4449.
Itoh H et al. *Chemistry Letters* 2011, 40, 1007-1008.

(Continued)

*Primary Examiner* — Joseph R Kosack
(74) *Attorney, Agent, or Firm* — Meunier Carlin & Curfman, LLC

(57) ABSTRACT

Methods for the borylation of aromatic compounds using cobalt catalysts are provided.

37 Claims, No Drawings

(56) References Cited

OTHER PUBLICATIONS

Iverson et al. *J. Am. Chem. Soc.* 1999, 121, 7696-7697.
Chen et al. *Science* 2000, 287, 1995-1997.
Kawamorita et al. *J. Am. Chem. Soc.* 2009, 131, 5058.
Lipshutz, et al., *Organic Letters* 2008, 10, 4279.
Liskey et al. *Chemical Commununications* 2009, 37, 5603-5605.
Liskey et al. *J. Am. Chem. Soc.* 2010, 132, 11389-11391.
Maleczka et al. *Tetrahedron Letters* 2002, 43, 7087-7090.
Miyaura, N. and Suzuki, A. *Chem. Rev.* 1995, 95, 2457.
Mkhalid et al. *Chemical Reviews* 2010, 110, 890-931.
Obligacion et al. *J. Am. Chem. Soc.* 2013, 135, 19107-19110.
Obligacion et al. *J. Am. Chem. Soc.* 2014, 136, 4133-4136.
Obligacion et al. *Organic Letters* 2013, 15, 2680-2683.
Partridge et al. *Organic Letters* 2013, 15, 140-143.
Preshlock et al. *JACS* 2013, 135, 7572-7582.
Rahaim RJ and Maleczka RE. *Tetrahedron Letters*, 2002, 40, 8823-8826.
Robbins et al. *Organic Letters* 2012, 14, 4266-4269.
Roering et al. *Organic Lett.* 2012, 14, 3558.
Schlosser M. *Angewandte Chemie Int. Ed.* 2005, 44, 376-393.
Shimada et al. *Angewandte Chemie Int. Ed.* 2001, 40, 2168-2171.
Snieckus V. *Chemical Reviews* 1990, 90, 879-933.
Stanforth, S. P. *Tetrahedron* 1998, 54, 263.
Tajuddin et al. *Chemical Science* 2012, 3, 3505-3515.
Takagi et al. *Tetrahedron Letters* 2002, 43, 5649-5654.
Tilly et al. *Tetrahedron Letters* 2002, 43, 8347-8350.
Tse et al. *Organic Letters* 2001, 3, 2831-2833.
Tsukamoto, H.; Kondo, Y. *Org. Lett.* 2007, 9, 4227.
Vanchura et al. *Chemical Communications* 2010, 46, 7724-7726.
Wang et al. *Tetrahedron Letters* 1991, 32, 4883-4884.
Watanabe et al. *Chemical and Pharmaceutical Bulletin* 1983, 31, 2662-2668.
Whisler et al., *Angew. Chem. Int. Ed.* 2004, 43, 2206-2225.
Winkle et al. *Journal of Organic Chemistry* 1982, 47, 2101-2108.
Yu et al. *J. Am. Chem. Soc.* 2013, 135, 13168-13184.
Harrisson, P., et a. "Microwave-Accelerated Iridium-Catalyzed Borylation of Aromatic C—H Bonds", Organic Letters, 14(23) 6012-6015 CODEN: ORLEF7; ISSN: 1523-7052, vol. 11, No. 16, Aug. 20, 2009, pp. 3586-3589.
Ishiyama, T. et al., "Room temperature borylation of arenes and heteroarenes using stoichiometric amounts of pinacolborane catalyzed by iridium complexes in an inert solvent" Electronic supplementary information (ESI) available: experimental procedures and spectral analyses of products. See http://www.rsc.org/suppdata/cc/b, Chemical Communications—CHEMCOM., No. 23, Jan. 1, 2003 (Jan. 1, 2003), p. 2924, XP55342856, ISSN: 1359-7345, DOI: 10.1039/b311103b, Scheme 2; table 1.
Ishiyama, T., et al. "Ortho-C—H borylation of benzoate esters with bis(pinacolato)diboron catalyzed by iridium-phosphine complexes", Chem. Commun., vol. 46, pp. 159-161.
Murphy, J.M., et al. "One-Pot Synthesis of Arylboronic Acids and Aryl Trifuroborates by Ir-Catalyzed Borylation of Arenes", Organic Letters, 14(23), 6012-6015 CODEN: ORLEF7; ISSN: 1523-7052, vol. 9, No. 5, Mar. 1, 2007 pp. 757-760, XP55342972, ISSN: 1523-7060, DOI: 10.1021/016062903o tables 1, 2, 3.
Extended European Search Report dated Mar. 21, 2017 in European Application 14843029.1 (9 pages).
Extended European Search Report dated Jan. 23, 2018 in European Application 15809975.4 (9 pages).
Adams et al. "Symthesis and reactivity of cobalt boryl complexes," Dalton Transactions, 2006, 1370-1373.
Zhang et al. "A Cobalt-Catalyzed Alkene Hydroboration with Pinacolborane," Angewandte Chemie Int. Ed. 2014, 53, 2696-2700.

METHODS FOR PRODUCING BORYLATED ARENES

CROSS REFERENCE TO RELATED APPLICATIONS

This application claims the benefit of U.S. Provisional Patent Application Ser. No. 62/012,681 filed Jun. 16, 2014, which is expressly incorporated by reference herein.

TECHNICAL FIELD

This application relates generally to methods of forming borylated arenes, as well as methods of using thereof.

BACKGROUND

Arylboronic acids and arylboronic acid esters are versatile reagents in organic chemistry. In particular, arylboronic acids and arylboronic acid esters can participate in a variety of cross-coupling reactions, such as Suzuki-type cross-coupling reactions, which can result in carbon-carbon bond formation, as generally illustrated below.

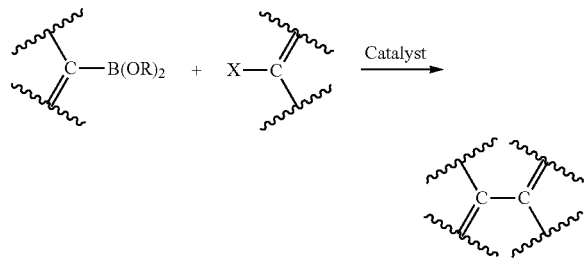

As a consequence, arylboronic esters and arylboronic acids are frequently key intermediates in the synthesis of highly functionalized organic compounds, including pharmaceuticals and agrochemicals. Improved methods for preparing arylboronic acids and arylboronic acid esters, including regioselective methods of preparing substituted arylboronic acids and substituted arylboronic acid esters, offer the potential to improve synthesis of important classes of organic compounds, including pharmaceuticals and agrochemicals.

SUMMARY

Metal-catalyzed C—H activation-borylation can be used to prepare arylboronic acids and arylboronic acid esters from their aromatic precursor in a single step. Metal-catalyzed C—H activation-borylation offers many advantages relative to alternative methods of borylation. For example, metal-catalyzed C—H activation-borylation does not require the cryogenic reaction temperatures that are typically required when using classical lithium-hydrogen exchange reactions to activate the C—H position for borylation. However, the metal-catalyzed C—H activation borylation typically employs costly iridium and rhodium catalyst systems. Provided herein are methods for the C—H activation-borylation of aromatic compounds that employ cobalt catalyst systems. The cobalt catalyst systems can be significantly less expensive than the costly iridium and rhodium catalyst systems typically employed for C—H activation-borylation.

Provided are methods for preparing borylated aromatic compounds. Methods for preparing a borylated aromatic compound can comprise contacting an aromatic substrate with a catalytic cobalt complex and a borylation reagent under conditions effective to form the borylated aromatic compound.

The aromatic substrate can be any suitable aromatic compound that can be subjected to C—H activation-borylation. For example, the aromatic substrate can be a substituted or unsubstituted aryl compound (e.g., a substituted or unsubstituted benzene), a substituted or unsubstituted six-membered heteroaromatic compound (e.g., a substituted or unsubstituted pyridine), or a substituted or unsubstituted five-membered heteroaromatic compound (e.g., a substituted or unsubstituted pyrrole, a substituted or unsubstituted furan, or a substituted or unsubstituted thiophene).

In these methods, the catalytic cobalt complex can be any suitable cobalt(I) or cobalt(II) complex that can catalyze the C—H activation-borylation of the aromatic substrate. In certain embodiments, the catalytic cobalt complex is a cobalt(I) complex.

In some embodiments, the catalytic cobalt complex can comprise a cobalt chelate complex comprising a tridentate ligand. For example, the catalytic cobalt complex can be a cobalt pincer complex. In some cases, the catalytic cobalt complex can be a cobalt chelate complex comprising a CCC, CNC, CNS, NNN, NCN, PCP, PNP, PCN, OCO, SCS, SNS, or SPS pincer ligand. In certain embodiments, the catalytic cobalt complex is not a cobalt chelate complex comprising an NNN or NPN pincer ligand. In certain embodiments, the catalytic cobalt complex is not one of the following:

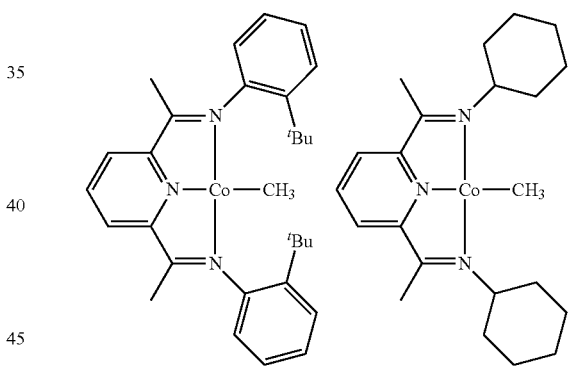

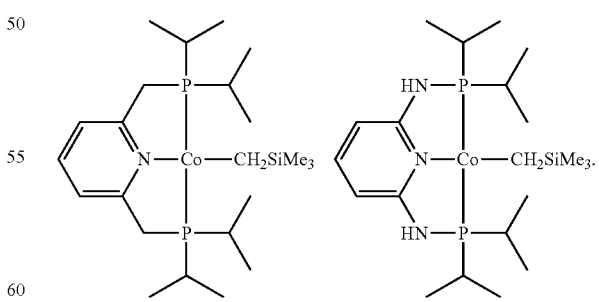

In certain embodiments, the catalytic cobalt complex is not a cobalt pincer complex. For example, the catalytic cobalt complex can comprise a cobalt chelate complex comprising a bidentate ligand, such as a complex defined by the formula below

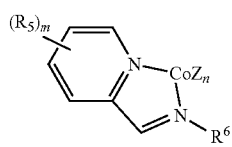

wherein

Z is, independently for each occurrence, a halide, a $C_1$-$C_6$ alkyl group, or an aryl group, n is 2, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, $R^6$ is selected from one of the following:

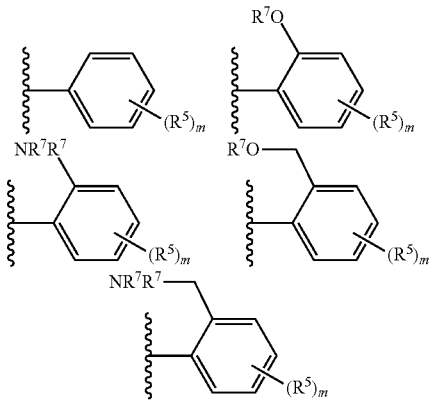

$R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt complex comprising exclusively monodentate ligands. For example, the catalytic cobalt complex can comprise $Py_2Co(CH_2SiMe_3)_2$.

In some embodiments, the catalytic cobalt complex can comprise a polymetallic cobalt complex, such as a bridged dicobalt complex. For example, the catalytic cobalt complex can comprise [(Cp*Co)$_2$-μ-($\eta^4$:$\eta^4$-toluene)].

Also provided are methods for borylating aromatic compounds having a ring substituent which includes a carbon atom in the alpha-position to the aromatic ring which is substituted with at least one hydrogen atom (e.g., at least two hydrogen atoms or three hydrogen atoms). The methods can include contacting the aromatic substrate with a catalytic cobalt complex and a borylation reagent under conditions effective to borylate the carbon atom in the alpha-position to the aromatic ring.

For example, provided are methods for preparing borylated compounds defined by Formula VII

Formula VII wherein X is a substituted or unsubstituted aryl group or a substituted or unsubstituted heteroaryl group, and Y is a boronic acid or a boronic acid derivative. The methods can include providing an aromatic substrate comprising a methyl-substituted aryl group or a methyl-substituted heteroaryl group and contacting the aromatic substrate with a catalytic cobalt complex and a borylation reagent under conditions effective to form a compound defined by Formula VII.

The aromatic substrate can comprise any suitable methyl-substituted aryl or methyl-substituted heteroaryl group. The aryl or heteroaryl group can optionally further comprise one or more substituents in addition to the methyl substituents. As a consequence, X can be any suitable substituted or unsubstituted aryl or heteroaryl group. For example, X can be a substituted or unsubstituted aryl group (e.g., a substituted or unsubstituted phenyl group). In other cases, X can be a substituted or unsubstituted heteroaryl group (e.g., a substituted or unsubstituted pyridyl group).

In certain embodiments, the aromatic substrate can comprise a compound defined by Formula VIII

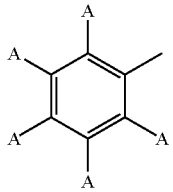

Formula VIII wherein

A is, individually for each occurrence, hydrogen, a halogen, —$OR^1$, —$NR^2R^3$, —$C(=O)R^4$, a nitrile group, a $C_1$-$C_6$ alkyl group, a $C_1$-$C_6$ haloalkyl group, or a boronic acid or a boronic acid derivative, $R^1$, $R^2$, and $R^3$ are each, individually for each occurrence, hydrogen or a $C_1$-$C_6$ alkyl group, and $R^4$ is, individually for each occurrence, hydrogen, —$OR^1$, —$NR^2R^3$, or a $C_1$-$C_6$ alkyl group.

In these embodiments, the borylated aromatic compound can comprise a compound defined by Formula IX

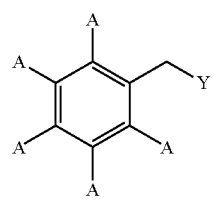

Formula IX wherein A is, for each occurrence, as described above and Y is a boronic acid or a boronic acid derivative. In certain cases, the borylated aromatic compound can comprise a compound defined by Formula IX, wherein Y is a boronic acid derivative selected from one of the following:

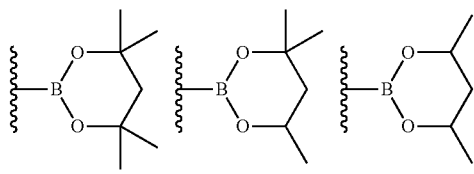

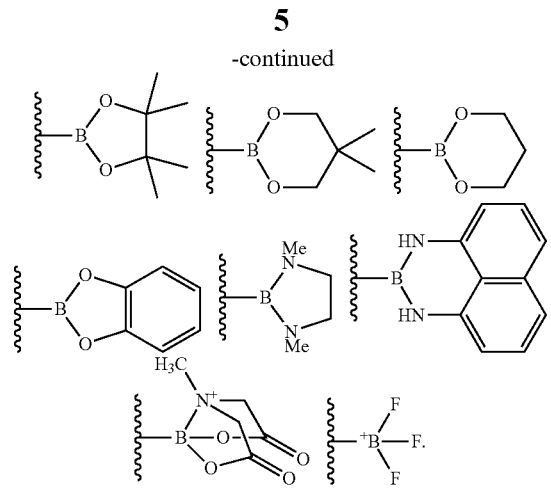

In these methods, the catalytic cobalt complex can be any suitable cobalt(I) or cobalt(II) complex that can catalyze the C—H activation-borylation of the aromatic substrate. In certain embodiments, the catalytic cobalt complex is a cobalt(II) complex.

In some embodiments, the catalytic cobalt complex can comprise a cobalt chelate complex comprising a tridentate ligand. For example, the catalytic cobalt complex can be a cobalt pincer complex. In some cases, the catalytic cobalt complex can be a cobalt chelate complex comprising a CCC, CNC, CNS, NNN, NCN, PCP, PNP, PCN, OCO, SCS, SNS, or SPS pincer ligand. In certain embodiments, the catalytic cobalt complex is not a cobalt chelate complex comprising an NNN or NPN pincer ligand. In certain embodiments, the catalytic cobalt complex is not one of the following:

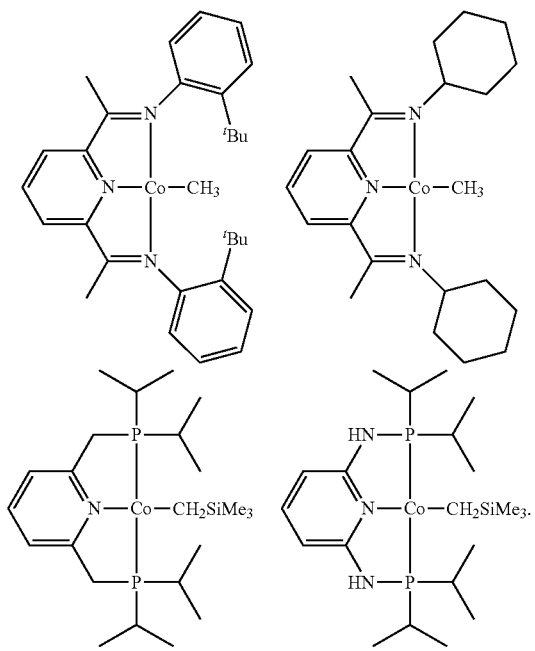

In certain embodiments, the catalytic cobalt complex is not a cobalt pincer complex. For example, the catalytic cobalt complex can comprise a cobalt chelate complex comprising a bidentate ligand, such as a complex defined by the formula below

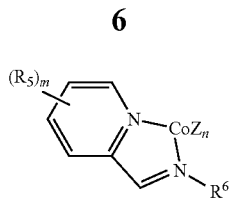

wherein

Z is, independently for each occurrence, a halide, a $C_1$-$C_6$ alkyl group, or an aryl group, n is 2, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, $R^6$ is selected from one of the following:

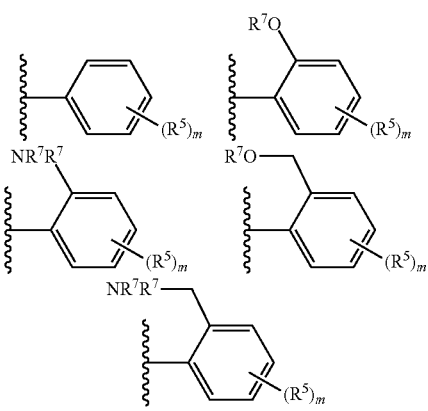

$R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt complex comprising exclusively monodentate ligands. For example, the catalytic cobalt complex can comprise $Py_2Co(CH_2SiMe_3)_2$.

In some embodiments, the catalytic cobalt complex can comprise a polymetallic cobalt complex, such as a bridged dicobalt complex. For example, the catalytic cobalt complex can comprise [(Cp*Co)$_2$-μ-($\eta^4$:$\eta^4$-toluene)].

The borylation reagent used in the methods described above can be any suitable HB or B—B organic compound known in the art as a borylation reagent. Suitable borylation reagents can be selected in view of a variety of factors, including considerations regarding the desired reactivity of the resulting borylated arenes. Exemplary borylation reagents include the HB or B—B organic compounds shown below.

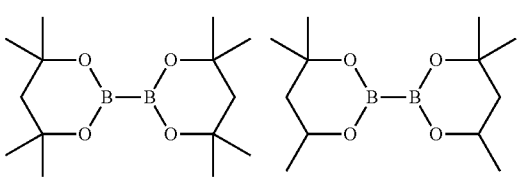

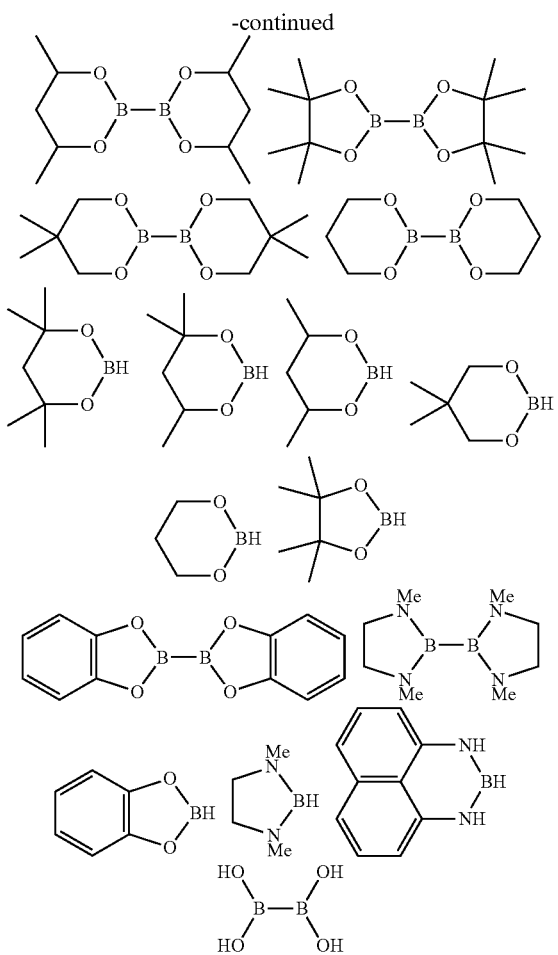

In some embodiments, the borylation reagent is selected from pinacolborane (HBPin), catecholborane, bis(neopentyl glycolato)diboron, bis(pinacolato)diboron ($B_2Pin_2$), bis(hexylene glycolato)diboron, and bis(catecholato)diboron. In certain embodiments, the borylation reagent is pinacolborane (HBPin) or bis(pinacolato)diboron ($B_2Pin_2$).

The borylated compounds prepared using the methods described herein can be utilized in additional chemical reactions, including cross-coupling reactions, such as Suzuki-type cross-coupling reactions. In some embodiments, the methods described herein can further comprise contacting the borylated aromatic compound with a reactant selected from the group consisting of an aryl halide, an aryl pseudohalide, a vinyl halide, and an vinyl pseudohalide, and a transition metal catalyst to cross-couple the borylated aromatic compound and the reactant.

DETAILED DESCRIPTION

Definitions

Terms used herein will have their customary meaning in the art unless specified otherwise. The organic moieties mentioned in the definitions of the variables of the formulae described herein are—like the term halogen—collective terms for individual listings of the individual group members. The prefix $C_n$-$C_m$ indicates in each case the possible number of carbon atoms in the group.

The term "alkyl," as used herein, refers to saturated straight, branched, cyclic, primary, secondary or tertiary hydrocarbons, including those having 1 to 6 carbon atoms. In some embodiments, alkyl groups will include $C_1$, $C_1$-$C_2$, $C_1$-$C_3$, $C_1$-$C_4$, $C_1$-$C_5$ or $C_1$-$C_6$ alkyl groups. Examples of $C_1$-$C_6$ alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and their isomers. $C_1$-$C_4$-alkyl groups can include, for example, methyl, ethyl, propyl, 1-methylethyl, butyl, 1-methylpropyl, 2-methylpropyl, and 1,1-dimethylethyl.

Cyclic alkyl groups or "cycloalkyl" groups, which are encompassed by alkyl include those with 3 to 6 carbon atoms having single or multiple condensed rings. In some embodiments, cycloalkyl groups include $C_4$-$C_6$ or $C_3$-$C_4$ cyclic alkyl groups. Non-limiting examples of cycloalkyl groups include cyclopropyl, cyclobutyl, cyclopentyl, and cyclohexyl groups.

Alkyl groups can be unsubstituted or substituted with one or more moieties, such as alkyl, halo, haloalkyl, hydroxyl, carboxyl, acyl, acyloxy, amino, alkyl- or dialkylamino, amido, nitro, cyano, azido, thiol, or any other viable functional group that does not preclude the synthetic methods described herein, either unprotected, or protected as necessary, as known to those skilled in the art, for example, as taught in Greene, et al., *Protective Groups in Organic Synthesis*, John Wiley and Sons, Third Edition, 1999, hereby incorporated by reference.

The term "haloalkyl," as used herein, refers to an alkyl group, as defined above, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "alkoxy," also defined as —OR where R is alkyl, refers to —O-alkyl, wherein alkyl is as defined above. Similarly, the term haloalkoxy can be used to refer to —O-haloalkyl, wherein haloalkyl is as defined above. In some embodiments, alkoxy groups can include 1 to 6 carbon atoms. Examples of $C_1$-$C_6$-alkoxy groups include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methylpropoxy.

The terms "alkylamino" and "dialkylamino" refer to alkyl-NH— and $(alkyl)_2N$— where alkyl is as defined above. Similarly, the terms haloalkylamino and halodialkylamino refer to haloalkyl-NH— and $(haloalkyl)_2$-NH—, where haloalkyl is as defined above. The term "aminoalkyl" refers to an alkyl group, as defined above, substituted with an amino group.

The terms "alkylcarbonyl," "alkoxycarbonyl," "alkylaminocarbonyl," and "dialkylaminocarbonyl" refer to —C(=O)-alkyl, —C(O)-alkoxy, —C(O)-alkylamino, and —C(O)— dialkylamino, where alkyl, alkoxy, alkylamino, and dialkylamino are as defined above.

The term "boronic acid," as used herein, refers to a —B(OH)$_2$ moiety. The term boronic acid derivative refers to boron-containing moieties which differ from boronic acid by the presence or absence of one or more atoms, functional groups, or substructures, and which can be imagined to be formed, at least theoretically, from boronic acid via some chemical or physical process. Examples of boronic acid derivatives include boronic acid esters, also referred to as boronates, boronate esters, or boronic esters; aminoboranes, including cyclic aminoboranes such as the 1,3,2-diazaborolidyl group; and boronic acid anhydrides. The term boronic acid ester refers to an esterified boronic acid moiety, such as —B(OR)$_2$ where R is an alkyl group as defined above, and cyclic boronic acid moieties represented by —B(OR)$_2$ wherein the two R substituents are linked together so as to form a $C_2$-$C_6$ cyclic moiety optionally including one or more additional heteroatoms (e.g., N, O, S, or combinations thereof), and optionally further substituted with one or more substituents and/or fused with (sharing at least one bond) one or more further carbocyclyl or heterocarbocyclyl groups. Examples of cyclic boronic esters include, but are not limited to, pinanediol boronic esters, pinacol boronic esters, 1,2-ethanediol boronic esters, 1,3-propanediol boronic esters, 1,2-propanediol boronic esters, 2,3-butanediol boronic esters, 1,1,2,2-tetramethylethanediol boronic esters, 1,2-diisopropylethanediol boronic esters, 5,6-decanediol boronic esters, 1,2-dicyclohexylethanediol boronic esters, bicyclohexyl-1,1'-diol boronic esters, diethanolamine boronic esters, and 1,2-diphenyl-1,2-ethanediol boronic esters.

The term "halogen" refers to the atoms fluorine, chlorine, bromine and iodine. The prefix halo- (e.g., as illustrated by the term haloalkyl) refers to all degrees of halogen substitution, from a single substitution to a perhalo substitution (e.g., as illustrated with methyl as chloromethyl (—CH$_2$Cl), dichloromethyl (—CHCl$_2$), trichloromethyl (—CCl$_3$)).

The term "aromatic compound" is used herein generally to refer to an aromatic ring or multiple aromatic rings that are fused together. Examples of aromatic compounds include, for example, benzene, naphthalene, anthracene, and the like. The term aromatic compound also includes heteroaromatic compounds (i.e., aromatic compounds in which one or more of the carbon atoms in the aromatic ring has been replaced by a heteroatom, such as O, N, or S). Examples of heteroaromatic compounds include, for example, pyridine, furan, indole, benzimidazole, thiophene, benzthiazole, and the like.

The term "aryl," as used herein, refers to a monovalent aromatic carbocyclic group of from 6 to 14 carbon atoms. Aryl groups can include a single ring or multiple condensed rings. In some embodiments, aryl groups include $C_6$-$C_{10}$ aryl groups. Aryl groups include, but are not limited to, phenyl, biphenyl, naphthyl, tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynylsulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynyl-sulfonyl, alkylamino, alkenylamino, alkynylamino, di(alkyl)amino, di(alkenyl)amino, di(alkynyl)amino, or trialkylsilyl.

The term "heteroaryl," as used herein, refers to a monovalent aromatic group of from 1 to 15 carbon atoms (e.g., from 1 to 10 carbon atoms, from 2 to 8 carbon atoms, from 3 to 6 carbon atoms, or from 4 to 6 carbon atoms) having one or more heteroatoms within the ring. The heteroaryl group can include from 1 to 4 heteroatoms, from 1 to 3 heteroatoms, or from 1 to 2 heteroatoms. In some cases, the heteroatom(s) incorporated into the ring are oxygen, nitrogen, sulfur, or combinations thereof. When present, the nitrogen and sulfur heteroatoms may optionally be oxidized. Heteroaryl groups can have a single ring (e.g., pyridyl or furyl) or multiple condensed rings provided that the point of attachment is through a heteroaryl ring atom. Preferred heteroaryls include pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, imidazolyl, oxazolyl, isoxazolyl, isothiazolyl, pyrazolyl, benzofuranyl, and benzothiophenyl. Heteroaryl rings may be unsubstituted or substituted by one or more moieties as described for aryl above.

Methods

Provided are methods for preparing borylated aromatic compounds. Methods for preparing a borylated aromatic compound can comprise contacting an aromatic substrate with a catalytic cobalt complex and a borylation reagent under conditions effective to form the borylated aromatic compound.

The aromatic substrate can be any suitable aromatic substrate that can be subjected to C—H activation-borylation. For example, the aromatic substrate can be a substituted or unsubstituted aryl compound (e.g., a substituted or unsubstituted benzene), a substituted or unsubstituted six-membered heteroaromatic substrate (e.g., a substituted or unsubstituted pyridine), or a substituted or unsubstituted five-membered heteroaromatic substrate (e.g., a substituted or unsubstituted pyrrole, a substituted or unsubstituted furan, or a substituted or unsubstituted thiophene).

In some cases, the aromatic substrate can comprise a phenyl ring. For example, the aromatic substrate can comprise a compound defined by Formula I

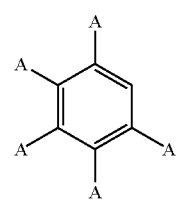

Formula I wherein

A is, individually for each occurrence, hydrogen, a halogen, —OR$^1$, —NR$^2$R$^3$, —C(=O)R$^4$, a nitrile group, a $C_1$-$C_6$ alkyl group, a $C_1$-$C_6$ haloalkyl group, or a boronic acid or a boronic acid derivative, R$^1$, R$^2$, and R$^3$ are each, individually for each occurrence, hydrogen or a $C_1$-$C_6$ alkyl group, and $R^4$ is, individually for each occurrence, hydrogen, —$OR^1$, —$NR^2R^3$, or a $C_1$-$C_6$ alkyl group.

In these embodiments, the borylated aromatic compound can comprise a compound defined by Formula II Formula II wherein A is, for each occurrence, as described above and Y is a boronic acid or a boronic acid derivative. In certain cases, the borylated aromatic compound can comprise a compound defined by Formula II, wherein Y is a boronic acid derivative selected from one of the following:

In some cases, the aromatic substrate can comprise a six-membered heteroaromatic compound. In certain cases, the aromatic substrate can comprise a six-membered heteroaromatic defined by one of Formula IIIa, Formula IIIb, or Formula IIIc Formula IIIa Formula IIIb Formula IIIc wherein
A is, individually for each occurrence, hydrogen, a halogen, —$OR^1$, —$NR^2R^3$, —$C(=O)R^4$, a nitrile group, a $C_1$-$C_6$ alkyl group, a $C_1$-$C_6$ haloalkyl group, or a boronic acid or a boronic acid derivative, $R^1$, $R^2$, and $R^3$ are each, individually for each occurrence, hydrogen or a $C_1$-$C_6$ alkyl group, and $R^4$ is, individually for each occurrence, hydrogen, —$OR^1$, —$NR^2R^3$, or a $C_1$-$C_6$ alkyl group.

In these embodiments, the borylated aromatic compound can comprise a compound defined by one of Formula IVa, Formula IVb, or Formula IVc Formula IVa Formula IVb Formula IVc wherein A is, for each occurrence, as described above and Y is a boronic acid or a boronic acid derivative. In certain cases, the borylated aromatic compound can comprise a compound defined by Formula IVa, Formula IVb, or Formula IVc, wherein Y is a boronic acid derivative selected from one of the following:

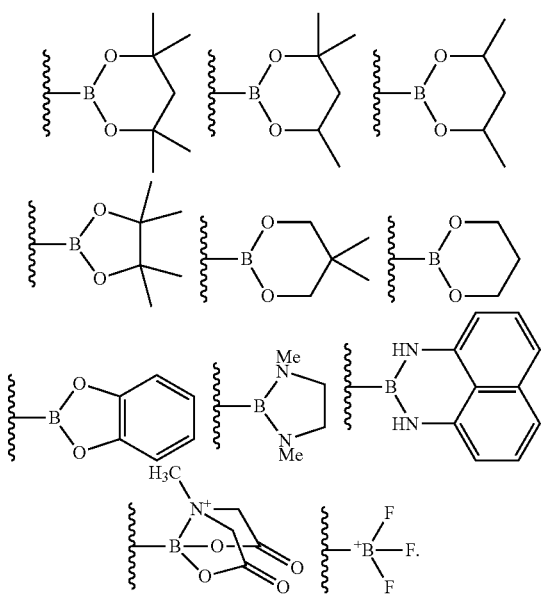

In some cases, the aromatic substrate can comprise a five-membered heteroaromatic compound. In certain cases, the aromatic substrate can comprise a five-membered heteroaromatic compound defined by one of Formula Va or Formula Vb

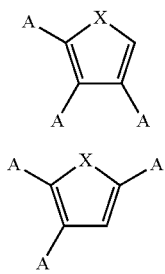

Formula Va

Formula Vb wherein

X is NH, O, or S;

A is, individually for each occurrence, hydrogen, a halogen, —OR$^1$, —NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group.

In these embodiments, the borylated aromatic compound can comprise a compound defined by one of Formula VIa or Formula VIb

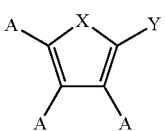

Formula VIa

Formula VIb wherein A is, for each occurrence, as described above and Y is a boronic acid or a boronic acid derivative. In certain cases, the borylated aromatic compound can comprise a compound defined by Formula VIa or Formula VIb, wherein Y is a boronic acid derivative selected from one of the following:

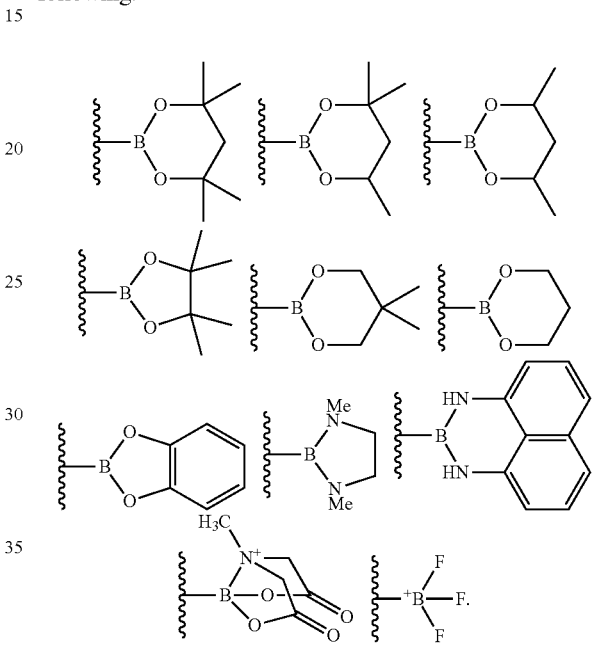

Percent conversion of the aromatic substrate to the borylated aromatic compound can vary depending on a number of factors, including the reactivity of the aromatic substrate, the identity of the catalytic cobalt complex, and the identity of the borylation reagent. In some embodiments, percent conversion of the aromatic substrate to the borylated aromatic compound can be at least 30% (e.g., at least 35%, at least 40%, at least 45%, at least 50%, at least 55%, at least 60%, at least 65%, at least 70%, at least 75%, at least 80%, at least 85%, at least 90%, or at least 95%).

The methods of forming borylated aromatic compounds described above can comprise contacting the aromatic substrate to be reacted with a catalytic cobalt complex and a borylation reagent. The aromatic substrate can be contacted with the catalytic cobalt complex and the borylation reagent in any suitable fashion, such that the aromatic substrate and the borylation reagent are present in combination with a catalytically effective amount of the catalytic cobalt complex. For example, the aromatic substrate can be contacted with the catalytic cobalt complex and the borylation reagent by combining in any order or fashion the aromatic substrate, the catalytic cobalt complex, and the borylation reagent in a single reaction vessel or solution (e.g., by sequential or simultaneous addition of the aromatic substrate, the catalytic cobalt complex, and the borylation reagent to a reaction vessel). In some embodiments, the aromatic substrate can be contacted with the catalytic cobalt complex and the borylation reagent at a temperature of from greater than 25° C. to 85° C.

The catalytic cobalt complex can be any suitable cobalt(I) or cobalt(II) complex that can catalyze the C—H activation-borylation of the aromatic substrate. In certain embodiments, the catalytic cobalt complex is a cobalt(I) complex.

In some embodiments, the catalytic cobalt complex can comprise a cobalt chelate complex comprising a tridentate ligand. For example, the catalytic cobalt complex can be a cobalt pincer complex. In some cases, the catalytic cobalt complex can be a cobalt chelate complex comprising a CCC, CNC, CNS, NNN, NCN, PCP, PNP, PCN, OCO, SCS, SNS, or SPS pincer ligand. In certain embodiments, the catalytic cobalt complex is not a cobalt chelate complex comprising an NNN or NPN pincer ligand. In certain embodiments, the catalytic cobalt complex is not one of the following:

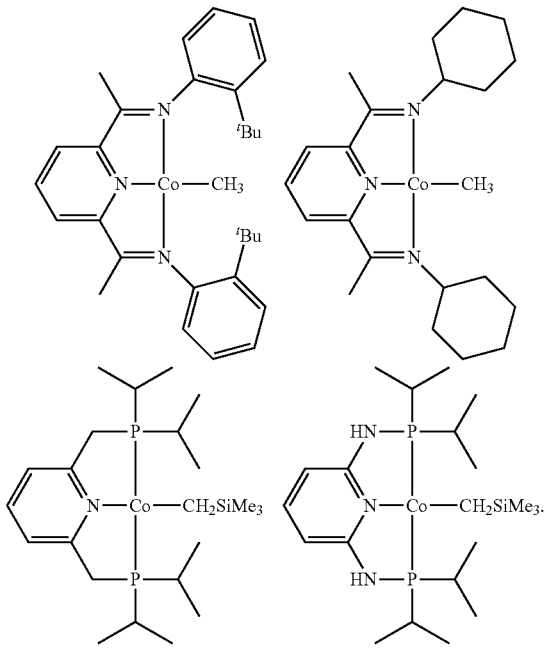

In certain embodiments, the catalytic cobalt complex is not a cobalt pincer complex.

In some embodiments, the catalytic cobalt complex can comprise a complex defined by the formula below

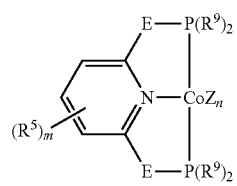

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —C(=O)$R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some of these embodiments, E can be chosen from —$CH_2$— and —$C(R^{10})_2$—, where $R^{10}$ is as defined above.

In some embodiments, the catalytic cobalt complex can comprise a complex defined by the formula below

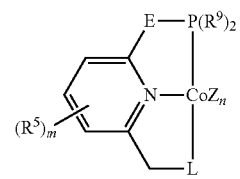

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —C(=O)$R^8$, a nitrile group, a $C_1$-$C_6$ alkyl group, an aryl group, or a $C_1$-$C_6$ haloalkyl group, m is 0, 1, 2, or 3, L is —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some embodiments, the catalytic cobalt complex can comprise a complex defined by the formula below

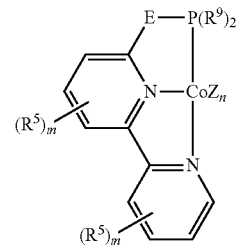

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —C(=O)$R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, $-OR^7$, $-NR^7R^7$, or a $C_1$-$C_6$ alkyl group, $R^9$ is, individually for each occurrence, a $C_1$-$C_6$ alkyl group, an aryl group, or $-OR^{10}$, and $R^{10}$ is, individually for each occurrence, a $C_1$-$C_6$ alkyl group or an aryl group.

In some of these embodiments, E can be chosen from $-CH_2-$ and $-C(R^{10})_2-$, where $R^{10}$ is as defined above.

In some embodiments, the catalytic cobalt complex can comprise a complex defined by the formula below

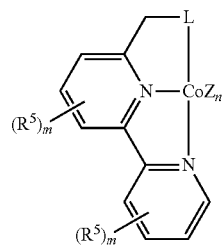

wherein

Z is, independently for each occurrence, a halide, a $C_1$-$C_6$ alkyl group, or an aryl group, n is 0, 1, 2, or 3, $R^5$ is, individually for each occurrence, a halogen, $-OR^7$, $-NR^7R^7$, $-C(=O)R^8$, a nitrile group, a $C_1$-$C_6$ alkyl group, an aryl group, or a $C_1$-$C_6$ haloalkyl group, m is 0, 1, 2, or 3, L is $-OR^{10}$ or $-NR^{10}R^{10}$, $R^7$ is, individually for each occurrence, hydrogen or a $C_1$-$C_6$ alkyl group, $R^8$ is, individually for each occurrence, hydrogen, $-OR^7$, $-NR^7R^7$, or a $C_1$-$C_6$ alkyl group, and $R^{10}$ is, individually for each occurrence, a $C_1$-$C_6$ alkyl group or an aryl group.

In some embodiments, the catalytic cobalt complex can comprise a complex defined by the formula below

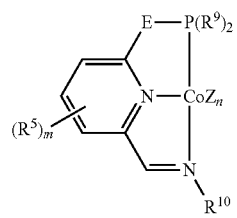

wherein

Z is, independently for each occurrence, a halide, a $C_1$-$C_6$ alkyl group, or an aryl group, n is 0, 1, 2, or 3, E is $-CH_2-$, $-C(R^{10})_2-$, $-NR^7-$, $-S-$, or $-O-$, $R^5$ is, individually for each occurrence, a halogen, $-OR^7$, $-NR^7R^7$, $-C(=O)R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, $-OR^7$, $-NR^7R^7$, or a $C_1$-$C_6$ alkyl group, $R^9$ is, individually for each occurrence, a $C_1$-$C_6$ alkyl group, an aryl group, or $-OR^{10}$, and $R^{10}$ is, individually for each occurrence, a $C_1$-$C_6$ alkyl group or an aryl group.

In some of these embodiments, E can be chosen from $-CH_2-$ and $-C(R^{10})_2-$, where $R^{10}$ is as defined above.

In some embodiments, the catalytic cobalt complex can comprise a complex defined by the formula below

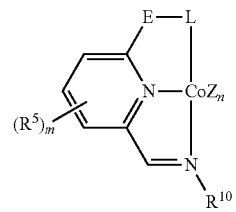

wherein

Z is, independently for each occurrence, a halide, a $C_1$-$C_6$ alkyl group, or an aryl group, n is 0, 1, 2, or 3, E is $-CH_2-$, $-C(R^{10})_2-$, $-NR^7-$, $-S-$, or $-O-$, $R^5$ is, individually for each occurrence, a halogen, $-OR^7$, $-NR^7R^7$, $-C(=O)R^8$, a nitrile group, a $C_1$-$C_6$ alkyl group, an aryl group, or a $C_1$-$C_6$ haloalkyl group, m is 0, 1, 2, or 3, L is $-OR^{10}$ or $-NR^{10}R^{10}$, $R^7$ is, individually for each occurrence, hydrogen or a $C_1$-$C_6$ alkyl group, $R^8$ is, individually for each occurrence, hydrogen, $-OR^7$, $-NR^7R^7$, or a $C_1$-$C_6$ alkyl group, and $R^{10}$ is, individually for each occurrence, a $C_1$-$C_6$ alkyl group or an aryl group.

In some of these embodiments, E can be chosen from $-CH_2-$ and $-C(R^{10})_2-$, where $R^{10}$ is as defined above.

In some embodiments, the catalytic cobalt complex can comprise a complex defined by the formula below

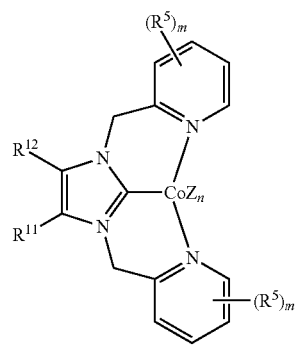

wherein

Z is, independently for each occurrence, a halide, a $C_1$-$C_6$ alkyl group, or an aryl group, n is 0, 1, 2, or 3, $R^5$ is, individually for each occurrence, a halogen, $-OR^7$, $-NR^7R^7$, $-C(=O)R^8$, a nitrile group, a $C_1$-$C_6$ alkyl group, an aryl group, or a $C_1$-$C_6$ haloalkyl group, m is 0, 1, 2, 3, or 4, $R^7$ is, individually for each occurrence, hydrogen or a $C_1$-$C_6$ alkyl group, $R^8$ is, individually for each occurrence, hydrogen, $-OR^7$, $-NR^7R^7$, or a $C_1$-$C_6$ alkyl group, and $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group.

In some embodiments, the catalytic cobalt complex can comprise a complex defined by the formula below

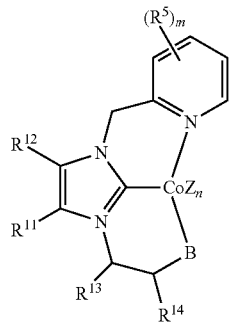

wherein

Z is, independently for each occurrence, a halide, a $C_1$-$C_6$ alkyl group, or an aryl group, n is 0, 1, 2, or 3, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, B is —$P(R^9)_2$, —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, $R^{10}$ is, individually for each occurrence, a $C_1$-$C_6$ alkyl group or an aryl group, $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, and $R^{13}$ and $R^{14}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{13}$ and $R^{14}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group.

In some embodiments, the catalytic cobalt complex can comprise a complex defined by the formula below

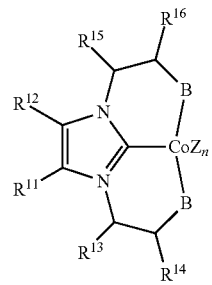

wherein

Z is, independently for each occurrence, a halide, a $C_1$-$C_6$ alkyl group, or an aryl group, n is 0, 1, 2, or 3, B is —$P(R^9)_2$, —$OR^{10}$ or —$NR^{10}R^{10}$, $R^9$ is, individually for each occurrence, a $C_1$-$C_6$ alkyl group, an aryl group, or —$OR^{10}$, $R^{10}$ is, individually for each occurrence, a $C_1$-$C_6$ alkyl group or an aryl group, $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, and $R^{13}$ and $R^{14}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{13}$ and $R^{14}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, $R^{15}$ and $R^{16}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{15}$ and $R^{16}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, $R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt chelate complex comprising a bidentate ligand. For example, in some embodiments, the catalytic cobalt complex can comprise a complex defined by the formula below

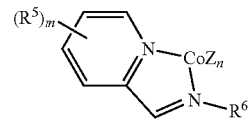

wherein

Z is, independently for each occurrence, a halide, a $C_1$-$C_6$ alkyl group, or an aryl group, n is 2, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, $R^6$ is selected from one of the following:

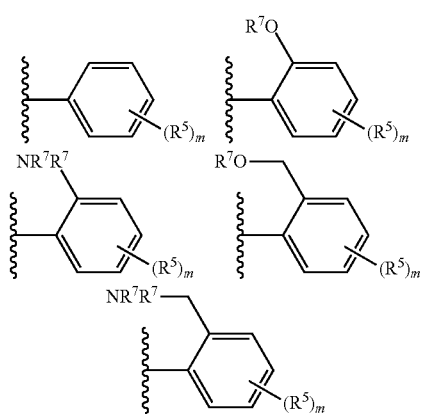

$R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt complex comprising exclusively monodentate ligands. For example, the catalytic cobalt complex can comprise $Py_2Co(CH_2SiMe_3)_2$. In some embodiments, the catalytic cobalt complex can comprise an N-heterocyclic carbene-ligated cobalt complex.

In some embodiments, the catalytic cobalt complex can comprise a polymetallic cobalt complex, such as a bridged dicobalt complex. For example, the catalytic cobalt complex can comprise $[(Cp*Co)_2\text{-}\mu\text{-}(\eta^4{:}\eta^4\text{-toluene})]$.

Methods can involve contacting the aromatic substrate with any catalytically effective amount of the catalytic cobalt complex. In some cases, the aromatic substrate can be contacted with from 0.5 mole percent (mol %) to 5.0 mol % of the catalytic cobalt complex (e.g., from 1.0 mol % to 3.0 mol %), based on the number of moles of the aromatic substrate present in the borylation reaction.

The borylation reagent can be any suitable HB or B—B organic compound known in the art as a borylation reagent. Suitable borylation reagents can be selected in view of a variety of factors, including considerations regarding the desired reactivity of the resulting borylated arenes. Exemplary borylation reagents include the HB or B—B organic compounds shown below.

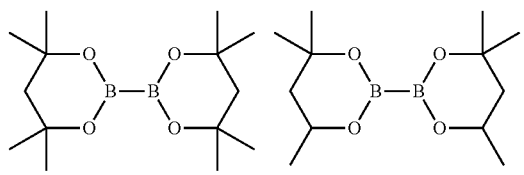

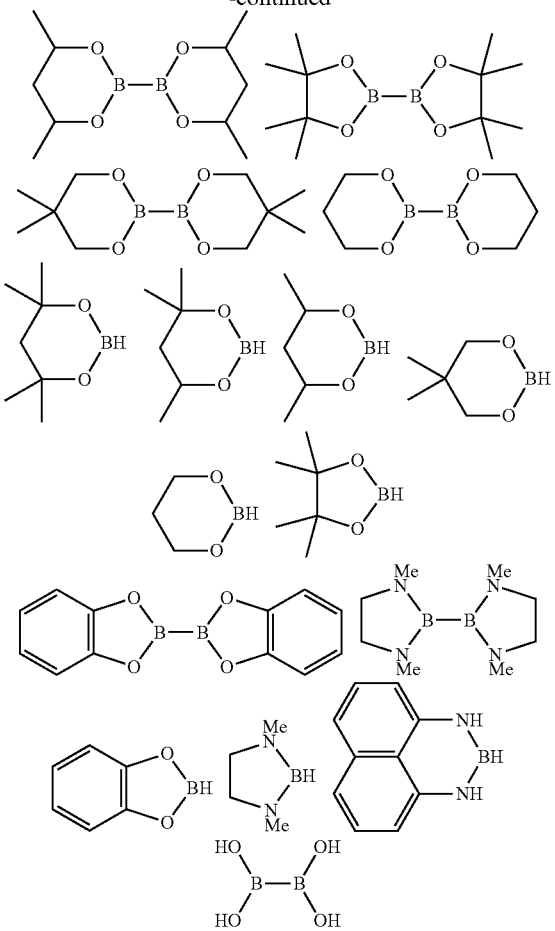

In some embodiments, the borylation reagent is selected from pinacolborane (HBPin), catecholborane, bis(neopentyl glycolato)diboron, bis(pinacolato)diboron ($B_2Pin_2$), bis(hexylene glycolato)diboron, and bis(catecholato)diboron. In certain embodiments, the borylation reagent is pinacolborane (HBPin) or bis(pinacolato)diboron ($B_2Pin_2$).

The borylation reagent can be incorporated in the borylation reaction in any suitable amount. For example, in some embodiments, the borylation reagent can be present in the borylation reaction in an amount ranging from 1 molar equivalent of borylation reagent per mole of aromatic substrate present in the borylation reaction to 5 molar equivalents of borylation reagent per mole of aromatic compound present in the borylation reaction (e.g., from 1 molar equivalent of borylation reagent per mole of aromatic substrate present in the borylation reaction to 3 molar equivalents of borylation reagent per mole of aromatic substrate present in the borylation reaction).

Also provided are methods for borylating aromatic compounds having a ring substituent which includes a carbon atom in the alpha-position to the aromatic ring which is substituted with at least one hydrogen atom (e.g., at least two hydrogen atoms, or three hydrogen atoms). The methods can include contacting the aromatic substrate with a catalytic cobalt complex and a borylation reagent under conditions effective to borylate the carbon atom in the alpha-position to the aromatic ring.

For example, provided are methods for preparing borylated compounds defined by Formula VII

Formula VII wherein X is a substituted or unsubstituted aryl group or a substituted or unsubstituted heteroaryl group, and Y is a boronic acid or a boronic acid derivative. The methods can include providing an aromatic substrate comprising a methyl-substituted aryl group or a methyl-substituted heteroaryl group; and contacting the aromatic substrate with a catalytic cobalt complex and a borylation reagent under conditions effective to form a compound defined by Formula VII.

The aromatic substrate can comprise any suitable methyl-substituted aryl or methyl-substituted heteroaryl group. The aryl or heteroaryl group can optionally further comprise one or more substituents in addition to the methyl substituents. As a consequence, X can be any suitable substituted or unsubstituted aryl or heteroaryl group. For example, X can be a substituted or unsubstituted aryl group, such as a substituted or unsubstituted phenyl, biphenyl, naphthyl, tetrahydronaphthyl, phenylcyclopropyl or indanyl group. In other cases, X can be a substituted or unsubstituted heteroaryl group, such as a substituted or unsubstituted pyridyl, pyridazinyl, pyrimidinyl, pyrazinyl, triazinyl, pyrrolyl, indolyl, quinolinyl, isoquinolinyl, quinazolinyl, quinoxalinyl, furanyl, thiophenyl, furyl, imidazolyl, oxazolyl, isoxazolyl, isothiazolyl, pyrazolyl benzofuranyl, or benzothiophenyl group. In certain embodiments, X is a substituted or unsubstituted phenyl or substituted or unsubstituted pyridyl group.

In certain embodiments, the aromatic substrate is a methyl-substituted aryl compound. The methyl-substituted aryl compound can optionally further comprise one or more substituents in addition to the methyl substituent. For example, the aromatic substrate can comprise a compound defined by Formula VIII

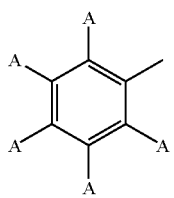

Formula VIII wherein

A is, individually for each occurrence, hydrogen, a halogen, —OR$^1$, —NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group.

In these embodiments, the borylated aromatic compound can comprise a compound defined by Formula IX

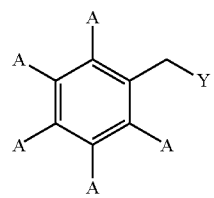

Formula IX wherein A is, for each occurrence, as described above and Y is a boronic acid or a boronic acid derivative. In certain cases, the borylated aromatic compound can comprise a compound defined by Formula IX, wherein Y is a boronic acid derivative selected from one of the following:

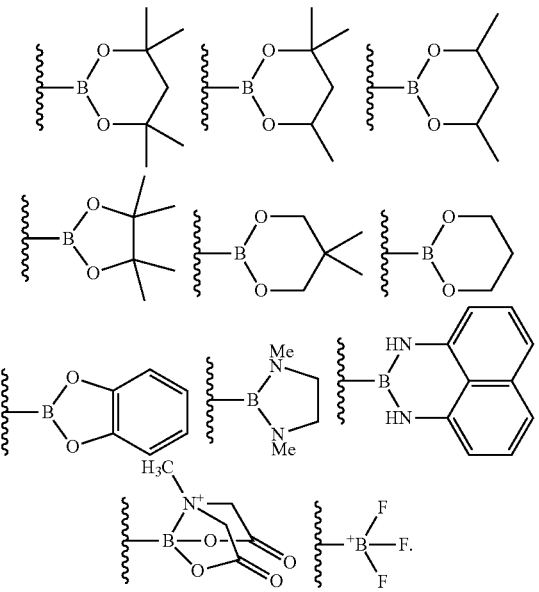

Percent conversion of the aromatic substrate to the borylated aromatic compound can vary depending on a number of factors, including the reactivity of the aromatic substrate, the identity of the catalytic cobalt complex, and the identity of the borylation reagent. In some embodiments, percent conversion of the aromatic substrate to the borylated aromatic compound can be at least 30% (e.g., at least 35%, at least 40%, at least 45%, at least 50%, at least 55%, at least 60%, at least 65%, at least 70%, at least 75%, at least 80%, at least 85%, at least 90%, or at least 95%).

The methods of forming borylated aromatic compounds described above can comprise contacting the aromatic substrate to be reacted with a catalytic cobalt complex and a borylation reagent. The aromatic substrate can be contacted with the catalytic cobalt complex and the borylation reagent in any suitable fashion, such that the aromatic substrate and the borylation reagent are present in combination with a catalytically effective amount of the catalytic cobalt complex. For example, the aromatic substrate can be contacted with the catalytic cobalt complex and the borylation reagent by combining in any order or fashion the aromatic substrate, the catalytic cobalt complex, and the borylation reagent in a single reaction vessel or solution (e.g., by sequential or simultaneous addition of the aromatic substrate, the catalytic cobalt complex, and the borylation reagent to a reaction vessel). In some embodiments, the aromatic substrate can be contacted with the catalytic cobalt complex and the borylation reagent at a temperature of from greater than 25° C. to 85° C.

The catalytic cobalt complex can be any suitable cobalt(I) or cobalt(II) complex that can catalyze the C—H activation-borylation of the aromatic substrate. In certain embodiments, the catalytic cobalt complex is a cobalt(II) complex.

In some embodiments, the catalytic cobalt complex can comprise a cobalt chelate complex comprising a tridentate ligand. For example, the catalytic cobalt complex can be a cobalt pincer complex. In some cases, the catalytic cobalt complex can be a cobalt chelate complex comprising a CCC, CNC, CNS, NNN, NCN, PCP, PNP, PCN, OCO, SCS, SNS, or SPS pincer ligand. In certain embodiments, the catalytic cobalt complex is not a cobalt chelate complex comprising an NNN or NPN pincer ligand. In certain embodiments, the catalytic cobalt complex is not one of the following:

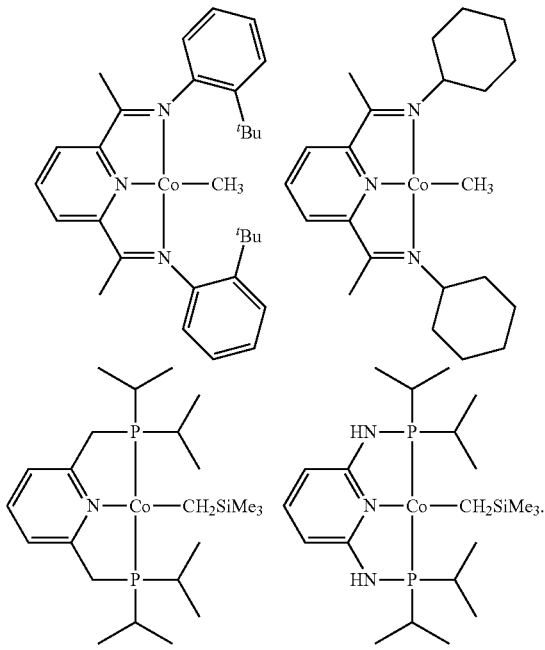

In certain embodiments, the catalytic cobalt complex is not a cobalt pincer complex.

In some embodiments, the catalytic cobalt complex can comprise a complex defined by the formula below

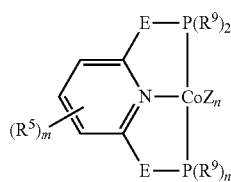

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some of these embodiments, E can be chosen from —$CH_2$— and —$C(R^{10})_2$—, where $R^{10}$ is as defined above.

In some embodiments, the catalytic cobalt complex can comprise a complex defined by the formula below

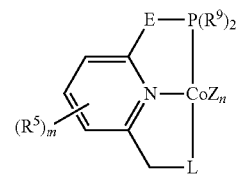

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, L is —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some embodiments, the catalytic cobalt complex can comprise a complex defined by the formula below

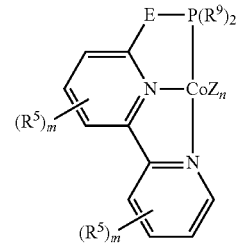

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some of these embodiments, E can be chosen from —$CH_2$— and —$C(R^{10})_2$—, where $R^{10}$ is as defined above.

In some embodiments, the catalytic cobalt complex can comprise a complex defined by the formula below

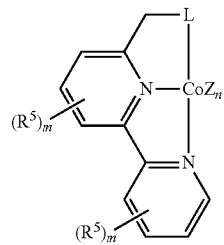

wherein

Z is, independently for each occurrence, a halide, a $C_1$-$C_6$ alkyl group, or an aryl group, n is 0, 1, 2, or 3, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, L is —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, and $R^{10}$ is, individually for each occurrence, a $C_1$-$C_6$ alkyl group or an aryl group.

In some embodiments, the catalytic cobalt complex can comprise a complex defined by the formula below

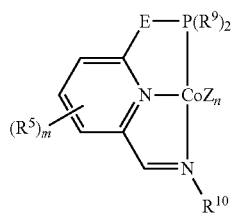

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, and $R^{10}$ is, individually for each occurrence, a $C_1$-$C_6$ alkyl group or an aryl group.

In some of these embodiments, E can be chosen from —$CH_2$— and —$C(R^{10})_2$—, where $R^{10}$ is as defined above.

In some embodiments, the catalytic cobalt complex can comprise a complex defined by the formula below

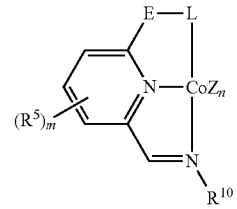

wherein

Z is, independently for each occurrence, a halide, a $C_1$-$C_6$ alkyl group, or an aryl group, n is 0, 1, 2, or 3, E is —$CH_2$—, —$C(R^{10})_2$—, —$NR^7$—, —S—, or —O—, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, or 3, L is —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, and $R^{10}$ is, individually for each occurrence, a $C_1$-$C_6$ alkyl group or an aryl group.

In some of these embodiments, E can be chosen from —$CH_2$— and —$C(R^{10})_2$—, where $R^{10}$ is as defined above.

In some embodiments, the catalytic cobalt complex can comprise a complex defined by the formula below

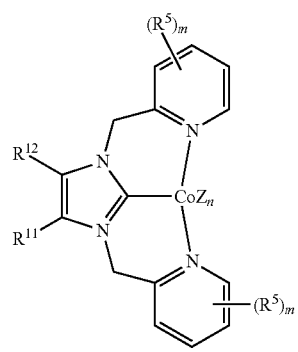

wherein

Z is, independently for each occurrence, a halide, a $C_1$-$C_6$ alkyl group, or an aryl group, n is 0, 1, 2, or 3, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, and $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group.

In some embodiments, the catalytic cobalt complex can comprise a complex defined by the formula below

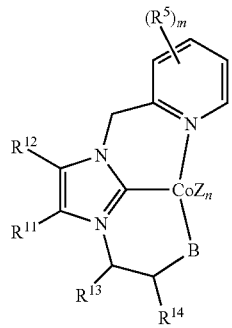

wherein

Z is, independently for each occurrence, a halide, a $C_1$-$C_6$ alkyl group, or an aryl group, n is 0, 1, 2, or 3, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, B is —$P(R^9)_2$, —$OR^{10}$ or —$NR^{10}R^{10}$, $R^7$ is, individually for each occurrence, hydrogen or a $C_1$-$C_6$ alkyl group, $R^8$ is, individually for each occurrence, hydrogen, —$OR^7$, —$NR^7R^7$, or a $C_1$-$C_6$ alkyl group, $R^9$ is, individually for each occurrence, a $C_1$-$C_6$ alkyl group, an aryl group, or —$OR^{10}$, $R^{10}$ is, individually for each occurrence, a $C_1$-$C_6$ alkyl group or an aryl group, $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, and $R^{13}$ and $R^{14}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{13}$ and $R^{14}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group.

In some embodiments, the catalytic cobalt complex can comprise a complex defined by the formula below

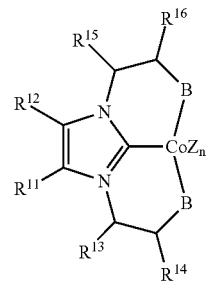

wherein

Z is, independently for each occurrence, a halide, a $C_1$-$C_6$ alkyl group, or an aryl group, n is 0, 1, 2, or 3, B is —$P(R^9)_2$, —$OR^{10}$ or —$NR^{10}R^{10}$, $R^9$ is, individually for each occurrence, a $C_1$-$C_6$ alkyl group, an aryl group, or —$OR^{10}$, $R^{10}$ is, individually for each occurrence, a $C_1$-$C_6$ alkyl group or an aryl group, $R^{11}$ and $R^{12}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{11}$ and $R^{12}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, and $R^{13}$ and $R^{14}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{13}$ and $R^{14}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, $R^{15}$ and $R^{16}$ are each individually selected from hydrogen, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, or $R^{15}$ and $R^{16}$, together with the carbon atoms to which they are attached, form a phenyl ring, optionally substituted with from 1 to 4 substituents individually selected from a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, $R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt chelate complex comprising a bidentate ligand. For example, in some embodiments, the catalytic cobalt complex can comprise a complex defined by the formula below

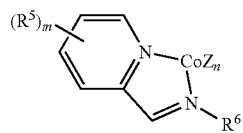

wherein

Z is, independently for each occurrence, a halide, a $C_1$-$C_6$ alkyl group, or an aryl group, n is 2, $R^5$ is, individually for each occurrence, a halogen, —$OR^7$, —$NR^7R^7$, —$C(=O)R^8$, a nitrile group, a $C_1$-$C_6$ alkyl group, an aryl group, or a $C_1$-$C_6$ haloalkyl group, m is 0, 1, 2, 3, or 4, $R^6$ is selected from one of the following:

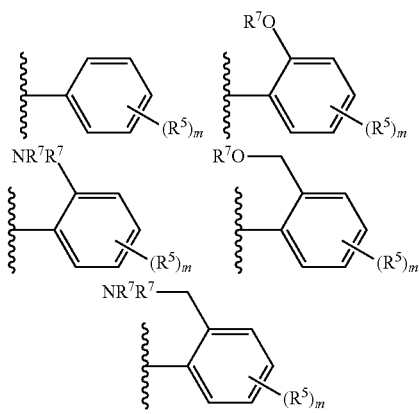

$R^7$ is, individually for each occurrence, hydrogen or a $C_1$-$C_6$ alkyl group, and $R^8$ is, individually for each occurrence, hydrogen, —$OR^7$, —$NR^7R^7$, or a $C_1$-$C_6$ alkyl group.

In some embodiments, the catalytic cobalt complex can comprise a cobalt complex comprising exclusively monodentate ligands. For example, the catalytic cobalt complex can comprise $Py_2Co(CH_2SiMe_3)_2$.

In some embodiments, the catalytic cobalt complex can comprise a bridged dicobalt complex. For example, the catalytic cobalt complex can comprise [(Cp*Co)$_2$-μ-(η$^4$:μ$^4$-toluene)].

Methods can involve contacting the aromatic compound with any catalytically effective amount of the catalytic cobalt complex. In some cases, the aromatic compound can be contacted with from 0.5 mol % to 5.0 mol % of the catalytic cobalt complex (e.g., from 1.0 mol % to 3.0 mol %), based on the number of moles of the aromatic compound present in the borylation reaction.

The borylation reagent can be any suitable HB or B—B organic compound known in the art as a borylation reagent. Suitable borylation reagents can be selected in view of a variety of factors, including considerations regarding the desired reactivity of the resulting borylated arenes. Exemplary borylation reagents include the HB or B—B organic compounds shown below.

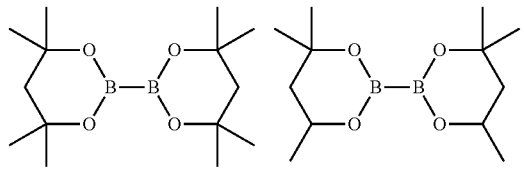

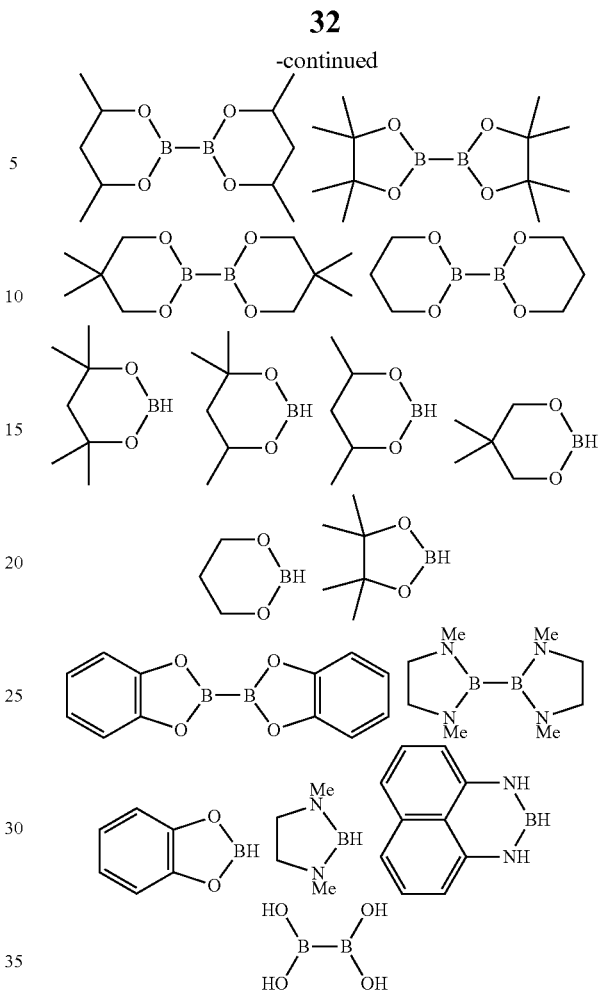

In some embodiments, the borylation reagent is selected from pinacolborane (HBPin), catecholborane, bis(neopentyl glycolato)diboron, bis(pinacolato)diboron ($B_2Pin_2$), bis(hexylene glycolato)diboron, and bis(catecholato)diboron. In certain embodiments, the borylation reagent is pinacolborane (HBPin) or bis(pinacolato)diboron ($B_2Pin_2$).

The borylation reagent can be incorporated in the borylation reaction in any suitable amount. For example, in some embodiments, the borylation reagent can be present in the borylation reaction in an amount ranging from 1 molar equivalent of borylation reagent per mole of aromatic substrate present in the borylation reaction to 5 molar equivalents of borylation reagent per mole of aromatic substrate present in the borylation reaction (e.g., from 1 molar equivalent of borylation reagent per mole of aromatic substrate present in the borylation reaction to 3 molar equivalents of borylation reagent per mole of aromatic substrate present in the borylation reaction).

Borylated arenes prepared using the methods described herein can be utilized in additional chemical reactions, including cross-coupling reactions, such as Suzuki-type cross-coupling reactions. Suzuki-type cross-coupling reactions are known in the art, and can be used to cross-couple an organohalide and an organoborane in the presence of a base and a suitable catalyst. See, for example, Miyaura, N. and Suzuki, A. *Chem. Rev.* 1995, 95, 2457, Stanforth, S. P. *Tetrahedron* 1998, 54, 263, Lipshutz, et al., *Synthesis* 2005, 2989, and Lipshutz, et al., *Organic Letters* 2008, 10, 4279. The organohalide can be an unsaturated halide or pseudohalide (e.g., a triflate (OTf)), such as an aryl halide or pseudohalide or vinyl halide or pseudohalide.

In some embodiments, the methods described herein can further comprise contacting the borylated aromatic compound with a reactant selected from the group consisting of an aryl halide, an aryl pseudohalide, a vinyl halide, and n vinyl pseudohalide, and a transition metal catalyst to cross-couple the reactant and the borylated aromatic compound. By way of example, a (4-chloro-2-fluoro-3-substituted)boronic acid ester can undergo a cross-coupling reaction with methyl 4-acetamido-3,6-dichloropicolinate to produce or form a 6-(4-chloro-2-fluoro-3-substituted-phenyl)-4-aminopicolinate. In another example, a (4-chloro-2-fluoro-3-substituted)boronic acid ester can undergo a cross-coupling reaction with methyl 6-acetamido-2-chloropyrimidine-4-carboxylate, or its unprotected analog the 6-amino-2-chloropyrimidine-4-carboxylic acid.

The Suzuki cross-coupling reaction can occur in the presence of a palladium catalyst, a ligand, and a base. In at least some embodiments, the palladium catalyst is palladium (II)acetate (Pd(OAc)$_2$), the base is aqueous potassium carbonate (K$_2$CO$_3$), and the ligand is triphenylphosphine (PPh$_3$). The cross-coupling reaction can be conducted in a solvent such as methyl isobutyl ketone (MIBK), acetonitrile (MeCN), ethyl acetate (EtOAc), water, or combinations thereof.

By way of non-limiting illustration, examples of certain embodiments of the present disclosure are given below.

EXAMPLES

Material and Methods

Unless otherwise specified, reactions were performed in oven-dried glassware under an atmosphere of nitrogen, with magnetic stirring, and monitored by proton nuclear magnetic resonance ($^1$H-NMR) spectroscopy. Tetrahydrofuran was freshly distilled from sodium/benzophenone under nitrogen. Py$_2$Co(CH$_2$SiMe$_3$)$_2$ and (Cp*Co)$_2$($\eta^4$:$\eta^4$-toluene) were synthesized according to established literature procedures. Flash or column chromatography was performed with silica gel (230-400 mesh) purchased from Silicycle (Quebec City, Canada). $^1$H NMR, $^{13}$C NMR and $^{19}$F NMR spectra were recorded using an Agilent DirectDrive2 500 MHz NMR spectrometer (500 MHz for $^1$H NMR, 125 MHz for $^{13}$C NMR, 470 MHz for $^{19}$F NMR and 160 MHz for $^{11}$B NMR) equipped with 7600AS 96 sample autosamplers running VnmrJ 3.2 A. Melting points were measured on a Thomas-Hoover capillary melting point apparatus.

Solvent Screening Using Py$_2$Co(CH$_2$SiMe$_3$)$_2$ as Catalyst

In a nitrogen filled glove box, a 3 milliliter (mL) Wheaton® vial was charged with Py$_2$Co(CH$_2$SiMe$_3$)$_2$ (9.8 milligrams (mg), 0.025 millimoles (mmol), 5 mol %) and m-xylene (306 microliters (μL), 2.5 mmol). The appropriate solvent (1.0 mL) and HBPin (73 μL, 0.5 mmol) were added sequentially. The vial was closed, placed into a 50° C. oil bath outside the glove box, and heated for 24 hours (h). The reaction was cooled to room temperature, and a sample was removed and analyzed by gas chromatography (GC). Results are represented in Table 1.

TABLE 1

Solvent Screening Using Py$_2$Co(CH$_2$SiMe$_3$)$_2$ as Catalyst.

| Entry | Solvent | 1:2 | mono:di | Yield$^a$ |
|---|---|---|---|---|
| 1 | none | 6.3:1 | 7.6:1 | 44% + diBPin |
| 2 | DMA | — | — | 0% |
| 3 | MeCN | — | — | 0% |
| 4 | THF | — | — | 4% |
| 5 | 1,4-dioxane | 12.2:1 | 5.7:1 | 12% + diBPin |
| 6 | DCM | — | — | 0% |
| 7 | DCE | — | — | 0% |
| 8 | CyH | 38.1:1 | 5.5:1 | 8% + diBPin |

$^a$Yields are calibrated GC yields.

Attempt of Using 3-Trifluoromethyltoluene as Substrate

In nitrogen filled glove box, a 3 mL Wheaton® vial was charged sequentially with Py$_2$Co(CH$_2$SiMe$_3$)$_2$ (9.8 mg, 0.025 mmol, 5 mol %), 3-trifluoromethyltoluene (349 μL, 2.5 mmol), and HBPin (73 μL, 0.5 mmol). The vial was closed, taken out of the glove box, and stirred at room temperature. After 16 h, a sample was taken from the reaction mixture and analyzed by GC. No borylation products were observed.

Borylation Attempt of Bromo- or Chloro-Containing Substrates with Py$_2$Co(CH$_2$SiMe$_3$)$_2$ as Catalyst In a nitrogen filled glove box, a 3 mL Wheaton® vial was charged sequentially with Py$_2$Co(CH$_2$SiMe$_3$)$_2$ (9.8 mg, 0.025 mmol, 5 mol %), 3-bromotoluene (303 μL, 2.5 mmol), and HBPin (73 μL, 0.5 mmol). The vial was closed, taken out of the glove box, and heated at 50° C. After 24 h, a sample was taken from the reaction mixture, and analysis by gas chromatography-mass spectrometry (GC-MS) of the sample showed the presence of borylation products arising from bromine-boron exchange in amounts stoichiometric in cobalt loadings. The chlorine-boron exchange product was observed by GC-MS in the crude reaction mixture when 2-chlorotoluene was used as substrate.

Screening of Solvents and Concentrations for Borylation of m-Xylene Using (Cp*Co)$_2$($\eta^4$:$\eta^4$-toluene) as Catalyst In a nitrogen filled glove box, 3 mL Wheaton® vials were charged with (Cp*Co)$_2$($\eta^4$:$\eta^4$-toluene) (12 mg, 0.025 mmol, 5 mol %) and B$_2$Pin$_2$ (127 mg, 0.5 mmol). The appropriate solvents (1.0 mL) and m-xylene (306 μL, 2.5 mmol) were added sequentially. The vials were closed, capped, taken out of the glove box, and heated at 80° C. for 24 h. Afterwards reaction vials were cooled to room temperature and samples were taken from the reaction mixtures for GC analysis. Results are represented in Table 2. The effect of concentration was assessed using the same conditions, but varying the volume of THF (Table 2). It was found that, by increasing the concentration of reactants, conversion increases, however, selectivity for aromatic borylation decreases.

TABLE 2

Screening of Solvents and Concentrations for Borylation of m-Xylene Using $(Cp*Co)_2(\eta^4{:}\eta^4\text{-toluene})$ as Catalyst.

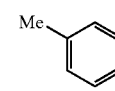

| Entry | Solvent (1.0 mL) | 1:2 | Yield[a] |
|---|---|---|---|
| 1 | none | 1:8.0 | 52% |
| 2 | DMA | — | 2% |
| 3 | MeCN | — | 0% |
| 4 | THF | 1:13.2 | 21% |
| 5 | THF (0.5 mL) | 1:11.2 | 38% |
| 6[b] | THF (0.25 mL) | 1:10.7 | 68% |
| 7 | 1,4-dioxane | 1:12.6 | 16% |
| 8[b] | MeTHF (0.25 mL) | 1:10.3 | 54% |
| 9[b] | MTBE (0.25 mL) | 1:10.5 | 30% |
| 10[b] | CpME (0.25 mL) | 1:10.4 | 24% |
| 11 | DCE | — | 0% |
| 12 | CyH | 1:10 | 7% |

[a]Yields are calibrated GC yields.
[b]Reaction conducted for 18 h.

Screening of External Ligands for m-Xylene Borylation Using $(Cp*Co)_2(\eta^4{:}\eta^4\text{-Toluene})$ In a nitrogen filled glove box, 3 mL Wheaton® vials were charged with $(Cp*Co)_2(\eta^4{:}\eta^4\text{-toluene})$ (12 mg, 0.025 mmol, 5 mol %), $B_2Pin_2$ (127 mg, 0.5 mmol), and one of the following ligands: $Ph_3P$ (6.6 mg, 0.025 mmol, 5 mol %), 4-(dimethylamino)pyridine (DMAP; 3.0 mg, 0.025 mmol, 5 mol %), 1,10-phenanthroline (phen; 2.2 mg, 0.0125 mmol, 2.5 mol %), tricyclohexylphosphine (Cy3P; 7.0 mg, 0.025 mmol, 5 mol %), or pyridine (Py; 2.0 µL, 0.025 mmol, 5 mol %). Tetrahydrofuran (1.0 mL) and m-xylene (306 µL, 2.5 mmol) were added sequentially. The vials were closed, capped, taken out of the glove box, and heated at 80° C. for 24 h. After heating was finished, the reaction vials were cooled to room temperature, and samples were taken from the reaction mixtures for GC analysis. Results are shown in Table 3.

TABLE 3

Screening of External Ligands for m-Xylene Borylation Using $(Cp*Co)_2(\eta^4{:}\eta^4\text{-toluene})$

| Entry | Ligand | Yield[a] |
|---|---|---|
| 1 | $Ph_3P$ | 0% |
| 2 | DMAP | 1% |
| 3 | phen | 2% |
| 4 | Py | 0% |
| 5 | $Cy_3P$ | 8% |

[a]Yields are calibrated GC yields.

Borylation Attempt of Methyl 3-Trifluoromethylbenzoate

In a nitrogen filled glove box, a 3 mL Wheaton® vial was charged with $(Cp*Co)_2(\eta^4{:}\eta^4\text{-toluene})$ (12 mg, 0.025 mmol, 5 mol %) and $B_2Pin_2$ (127 mg, 0.5 mmol). Tetrahydrofuran (0.5 mL) and methyl 3-trifluoromethylbenzoate (236 µL, 1.5 mmol) were added sequentially. The vial was capped, taken out of the glove box, and heated at 80° C. for 17 h. After heating was finished, the reaction vial was cooled to room temperature, and a sample was taken for analysis. GC analysis shows no presence of borylation product.

Borylation of 3-Fluorotoluene Using $(Cp*Co)_2(\eta^4{:}\eta^4\text{-toluene})$

In a nitrogen filled glove box, a 3 mL Wheaton® vial was charged with $(Cp*Co)_2(\eta^4{:}\eta^4\text{-toluene})$ (12 mg, 0.025 mmol, 5 mol %) and $B_2Pin_2$ (127 mg, 0.5 mmol). Tetrahydrofuran (0.5 mL) and 3-fluorotoluene (167 µL, 1.5 mmol) were added sequentially. The vial was capped, taken out of the glove box, and heated at 80° C. for 21 h. After heating was finished, the reaction vial was cooled to room temperature, and a sample was taken for analysis. Conversion of 25% (based on $B_2Pin_2$) was observed as judged from $^{19}$F-NMR spectra. The ratio of 2-(3-fluoro-5-methylphenyl)-4,4,5,5-tetramethyl-1,3,2-dioxaborolane to 2-(2-fluoro-4-methylphenyl)-4,4,5,5-tetramethyl-1,3,2-dioxaborolane was determined to be 1.4:1 from $^{19}$F-NMR spectra. 2-(3-Fluoro-5-methylphenyl)-4,4,5,5-tetramethyl-1,3,2-dioxaborolane: $^{19}$F NMR (283 MHz, $CDCl_3$) δ −115.4. 2-(2-Fluoro-4-methylphenyl)-4,4,5,5-tetramethyl-1,3,2-dioxaborolane: $^{19}$F NMR (283 MHz, $CDCl_3$) δ −103.8−−103.9.

Screening of External Ligands for m-Xylene Borylation Using $CoCl_2$ and Zn

Cobalt-based systems including various phosphine- or nitrogen-containing ligands were evaluated for borylation m-xylene borylation using the general procedure outlined in Scheme 1. In a nitrogen filled glove box, a 3 mL Wheaton® vial was charged with $CoCl_2$ (6.5 mg, 0.05 mmol, 10 mol %), ligand (0.05 mmol, 10 mol %), and Zn powder (9.8 mg, 0.15 mmol, 30 mol %). 1.0 mL of THF was then added. To the resulting solution, m-xylene (183 µL, 1.5 mmol) and the boron source (0.5 mmol) were added sequentially. The vial was then capped and taken out of the glove box. The reaction mixture was heated at 80° C. for 16-20 h. After heating, an aliquot was removed and analyzed via gas chromatography. In all cases, no borylated products were detected.

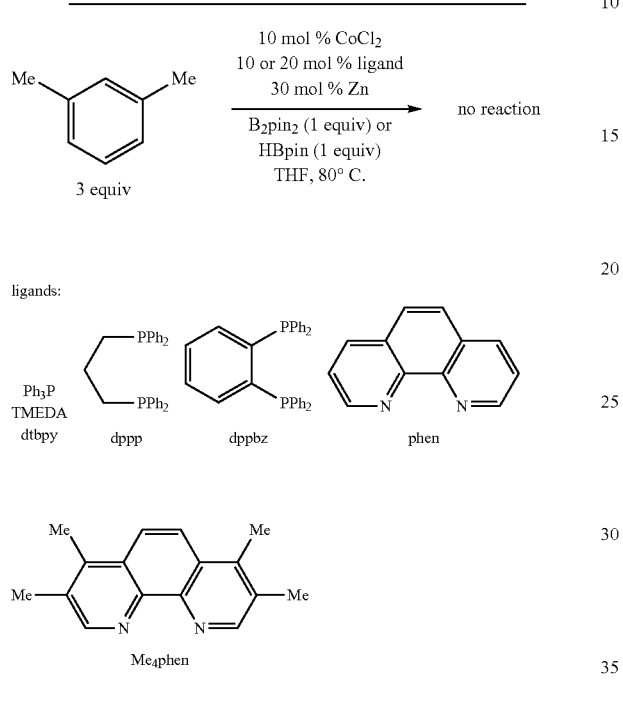

Borylation Using Cobalt Complexes Including a Bidentate Ligand

Cobalt complexes including a bidentate ligand containing both a pyridine moiety and an imine moiety were evaluated as catalysts for borylations. Ligands of this type are accessible through condensation of 2-pyridinecarboxyaldehyde with an appropriate aniline. Pyridylimine-ligated cobalt chloride complexes 1-4 were prepared using literature procedures. See, for example, Zhu, D. et al. *Organometallics* 2010, 29, 1897. All complexes were isolated as chloride-bridged dimers. The chloride ligands could be replaced to activate these complexes towards borylation.

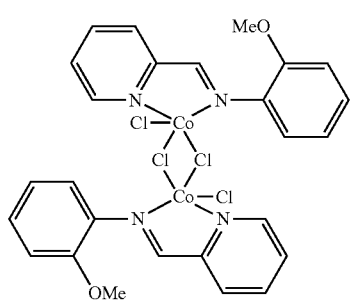

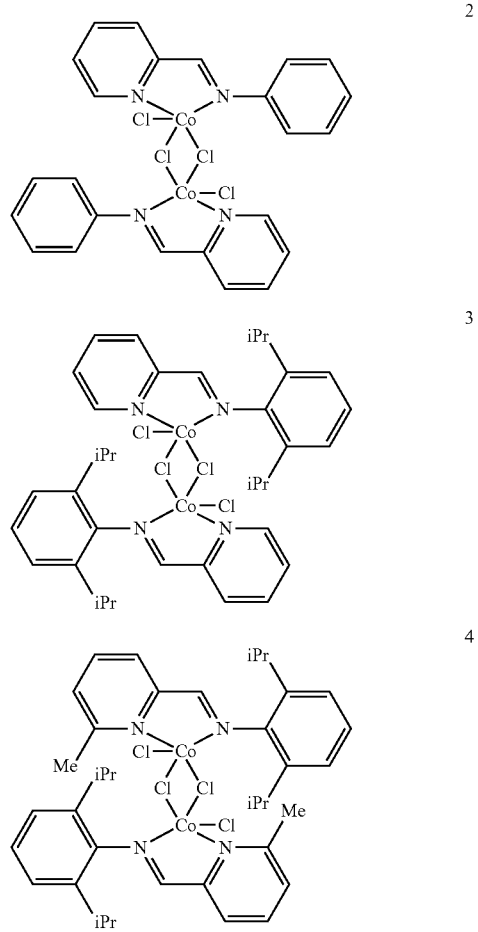

In a first experiment, the chloride ligands on cobalt complex 1 were substituted by reaction with LiCH$_2$TMS, forming complex 5. Complex 5 was then evaluated as a catalyst for the borylation of m-xylene. In a nitrogen filled glove box, a 3 mL Wheaton® vial was charged with cobalt complex 5 (11.1 mg, 0.025 mmol, 5 mol %) and m-xylene (183 μL, 1.5 mmol). HBpin (73 μL, 0.5 mmol) was then added. The vial was capped and taken out of the glove box. The reaction mixture was then heated at 50° C. for 15 h. Analysis by gas chromatography showed 29% conversion based on HBpin. Although catalytically active, complex 5 was found to be unstable for prolonged storage.

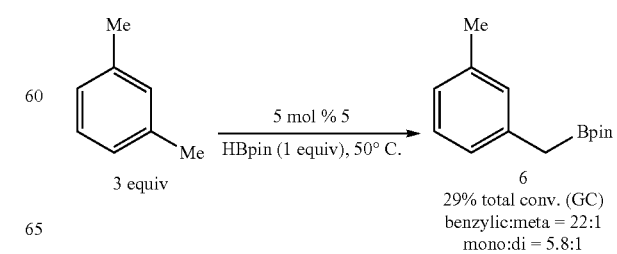

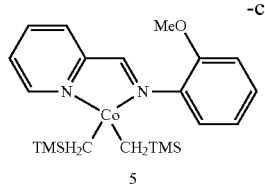

5

The activation of complexes 1-4 can also be accomplished using a reducing metal (e.g., magnesium or zinc) to reduce the cobalt center and remove one or both of the chloride ligands.

No borylation products were observed in an initial experiment using 2.5 mol % of 1, 12 mol % of Rieke's Mg, 3 eqiuv of m-xylene and HBpin (1 equiv) at 50° C. However, the reaction was run in THF at 80° C., 48% total conversion was obtained, with 41% being compound 6. Observed benzylic to meta borylation ratio was 27:1.

Somewhat lower total conversion (38%) was detected by GC when complex 3 was used as catalyst under identical conditions (Scheme 3). Specifically, in a nitrogen filled glove box, a 3 mL Wheaton® vial was charged with cobalt complex 3 (19.8 mg, 0.025 mmol, 2.5 mol %) and activated Mg (2.4 mg, 0.1 mmol, 10 mol %). 0.5 mL of THF was then added. The resulting mixture was stirred for 5 min. m-Xylene (367 µL, 3.0 mmol) and HBpin (145 µL, 1.0 mmol) were then added sequentially. The vial was capped and taken out of the glove box. The reaction mixture was then heated at 80° C. for 16 h. Analysis by GC showed 38% conversion based on HBpin, with 34% being identified as benzylic borylation product 6.

When zinc or Super-Hydride® (LiHBEt₃ 1.0M in THF) were used in place of magnesium, no borylation products were observed. An iron(II) bromide analog of cobalt complex 3 was also prepared and tested for activity in borylation reactions using Rieke's Mg. No borylation products were detected when m-xylene or 3-trifluorotoluene substrates were used.

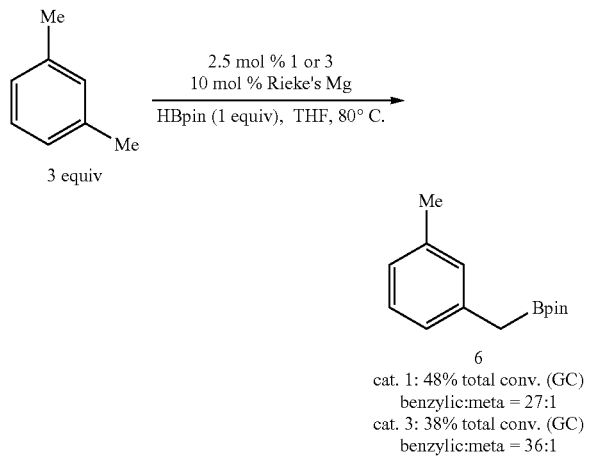

The activation of complexes 1-4 using a Grignard reagent was also investigated. In a first experiment, complex 1 and EtMgBr were evaluated as a catalytic system. m-Xylene was borylated in 42% total conversion. Again, benzylic borylation product 6 was the major product and was detected in 37% by GC (Scheme 4). Unfortunately, conversion rates over 3 runs varied from 0-42%.

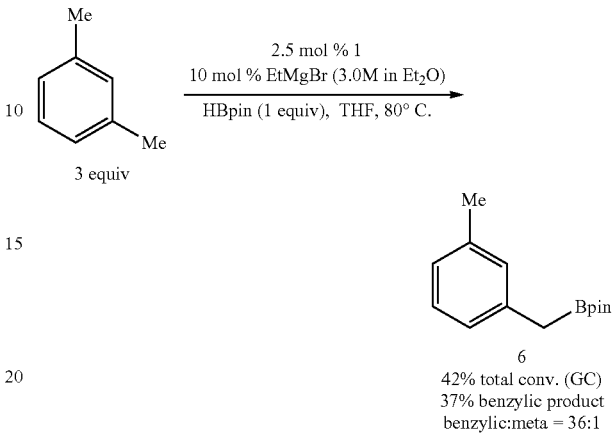

Using similar conditions, the activation of cobalt complex 3 with a variety of Grignard reagents was investigated. In a nitrogen-filled glove box, a 3 mL Wheaton® vial was charged with cobalt complex 3 (19.8 mg, 0.025 mmol, 2.5 mol %). THF (0.5 mL) and m-xylene (367 µL, 3.0 mmol) were added sequentially. Next, the Grignard reagent (0.1 mmol, 10 mol %) was added dropwise. The resulting mixture was then stirred for about 5 min. HBpin (145 µL, 1.0 mmol) was then added. The vial was capped and taken out of the glove box. The reaction mixture was heated at 80° C. for 21 h. After heating, an aliquot was removed and analyzed via gas chromatography. The results are included in Table 1 below.

Significant variation in borylation reaction outcome was observed when using EtMgBr as an activator. Over 6 runs, conversion rates ranging from 31-92% (Table 1, entry 2) were obtained. CyMgCl afforded conversion rates of 79-92% over 5 runs (Table 1, entry 4). In two trials performed using MeMgCl as an activator, conversion rates of 57-84% were observed (Table 1, entry 1). Low conversion was achieved with bulky tBuMgCl, and no borylated products were observed when PhMgCl was employed as catalyst activator.

TABLE 1

Borylation of m-xylene using cobalt complex 3 with various Grignard reagents as an activator

| entry | RMgX | Conversion | # of runs |
|---|---|---|---|
| 1 | MeMgCl | 57-84% (total) | 2 |
|   |        | 47-68% (benzylic) |   |
| 2 | EtMgBr | 31-92% (total) | 6 |
|   |        | 27-79% (benzylic) |   |
| 3 | EtMgCl | 79% (total) | 1 |
|   |        | 64% (benzylic) |   |

TABLE 1-continued

Borylation of m-xylene using cobalt complex 3 with various Grignard reagents as an activator

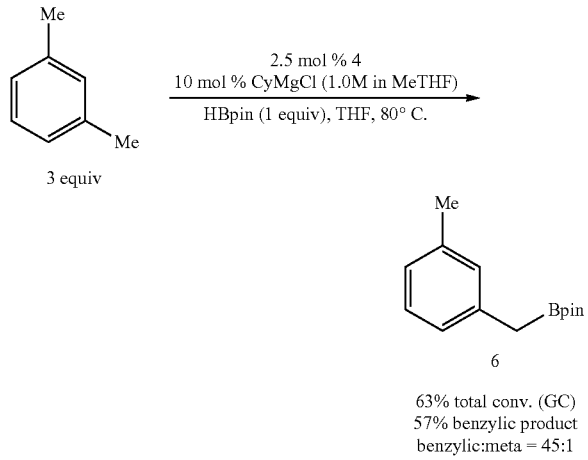

| entry | RMgX | Conversion | # of runs |
|---|---|---|---|
| 4 | CyMgCl | 79-91% (total) | 5 |
|   |        | 64-73% (benzylic) |   |
| 5 | tBuMgCl | 37% (total) | 1 |
|   |         | 31% (benzylic) |   |
| 6 | PhMgCl | no rxn | 1 |

Other organometallic reagents such as $Bu_2Mg$ or $Et_2Zn$ were also screened as potential reducing agents for use as activators with cobalt complex 3. When diethylzinc was used as catalyst activator, no borylation products were detected by GC. However, with di-n-butylmagnesium 75% conversion (62% benzylic borylation product 6) to borylated products from m-xylene was observed.

The activity of cobalt complex 4 (bearing a more bulky pyridylimine ligand) was compared to cobalt complex 3 in the borylation of m-xylene. A borylation reaction performed using cobalt complex 4 resulted in 63% total conversion, and borylated compound 6 was detected in 57% (Scheme 5). However, cobalt complex 4 afforded slightly lower conversion compared to catalyst 3. No significant differences were observed in selectivity.

Scheme 5. Borylation of m-xylene using cobalt catalyst 4 and CyMgCl as an activator

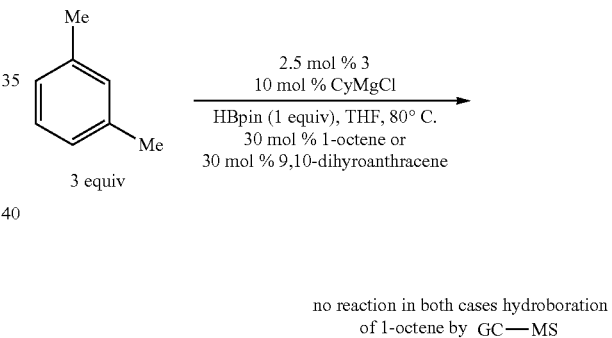

63% total conv. (GC)
57% benzylic product
benzylic:meta = 45:1

The amount of activating agent (e.g., Grignard reagent) and sequence of addition of reagents was found to influence the borylation reaction. No borylation products were found by GC if 5 or 20 mol % of Grignard reagent (e.g., EtMgBr and CyMgCl) was used. The order of reagent addition influenced the reaction outcome as well. In the case of the reactions described in Table 1, the catalyst was first suspended in THF and m-xylene. The Grignard reagent was then added slowly to the mixture. The resulting mixture was stirred for approximately 5 min; HBpin was then added to the reaction. However, if the order of addition of reagents was modified so that the Grignard reagent was the last reagent added to the reaction mixture (after HBpin), the overall reaction conversion decreased significantly (34% with EtMgBr; 13% with CyMgCl). The addition of pyridine as an external ligand was also found to shut down the reaction.

Investigation of the Borylation Mechanism

It was hypothesized that the borylation reaction could proceed by either a radical or ionic mechanism. If the borylation reaction were to proceed by a radical pathway, one would expect that the addition of radical scavengers to the borylation reaction should slow down or stop the reaction.

Borylation reactions were performed in the presence of 1-octene and 9,10-dihydroanthracene (Scheme 6). When alkene was present, additive hydroboration of 1-octene was detected by GC-MS, and no borylation products arising from m-xylene were observed. Similarly, no borylation products arising from m-xylene were observed when 9,10-dihydroanthracene was present. However, in this case, anthracene (the expected product of reaction of 9,10-dihydroanthracene with radical species) was not detected by GC or GC-MS either.

Scheme 6. Borylation reactons performed in the presence of 1-octene and 9,10-dihydroanthracene no reaction in both cases hydroboration of 1-octene by GC—MS To better elucidate the reaction mechanism, p-cymene was used as substrate for borylation. If borylation of p-cymene were to proceed through a radical intermediate, one would expect a balance between primary and tertiary radicals to be established during the reaction. One would expect this to result in formation of two borylated products.

In a first experiment, the borylation of p-cymene was performed using cobalt complex 3 and EtMgCl as activator. In a nitrogen-filled glove box, a 3 mL Wheaton® vial was charged with cobalt complex 3 (19.8 mg, 0.025 mmol, 2.5 mol %). Next, THF (0.5 mL) and p-cymene (468 µL, 3.0 mmol) were added. EtMgCl (2.0M in MeTHF) (50 µL, 0.1 mmol) was then added dropwise. The resulting mixture was then stirred for about 5 min. HBpin (145 µL, 1.0 mmol) was then added. The vial was capped and taken out of the glove box. The reaction mixture was heated at 80° C. for 21 h. Analysis by GC showed 19% conversion to a single isomer based on HBpin (Scheme 7). Performing this reaction using CyMgCl or MeMgCl as an activator afforded no borylation products.

Scheme 7. Borylation of p-cymene with complex 3 using EtMgCl as activator

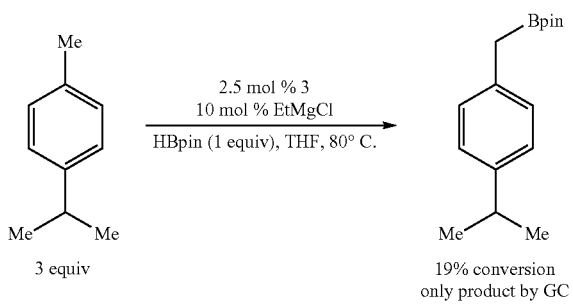

Next, a competition experiment was performed in which equimolar quantities of m-xylene and p-cymene were subjected to borylation (Scheme 8). In a nitrogen-filled glove box, a 3 mL Wheaton® vial was charged with cobalt complex 3 (19.8 mg, 0.025 mmol, 2.5 mol %). THF (0.5 mL), m-xylene (367 µL, 3.0 mmol), and p-cymene (468 µL, 3.0 mmol) were added. CyMgCl (1.0M in MeTHF) (100 µL, 0.1 mmol) was then added dropwise. The resulting mixture was then stirred for about 5 min. HBpin (145 µL, 1.0 mmol) was then added. The vial was capped and taken out of the glove box. The reaction mixture was heated at 80° C. for 21 h. Analysis by GC showed 72% conversion of m-xylene (based on HBpin) and 7% conversion of p-cymene (based on HBpin).

p-Cymene is good hydrogen atom donor that can form stable tertiary benzylic radicals through hydrogen atom transfer. Given that p-cymene did not shut down the borylation of m-xylene in the competition reaction, it is likely that these cobalt catalyzed borylations do not proceed via a radical pathway.

Scheme 8. Borylation of an equimolar m-xylene and p-cymene mixture with cobalt complex 3 using CyMgCl as activator

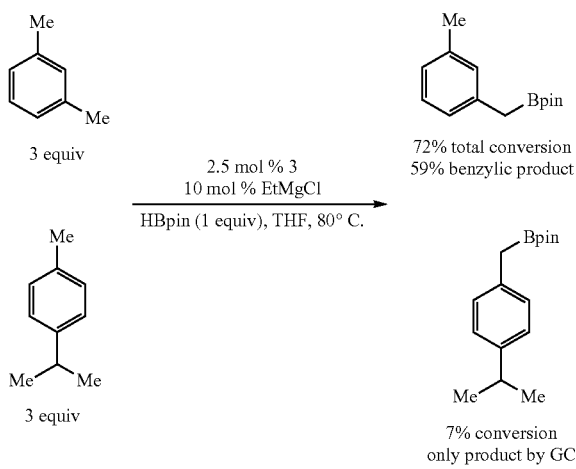

The fate of alkyl residue from the Grignard reagent was investigated using dodecylmagnesium bromide as an activator. Under catalytic reaction conditions, traces of dodecane were detected by GC and GC-MS. Quantification of dodecane was performed by GC analysis of an aliquot from a stoichiometric reaction between cobalt complex 3 and dodecylmagnesium bromide. Dodecane was formed in 70% yield from this stoichiometric reaction; however, other unidentified $C_{12}$-containing products were also detected by GC-MS.

Borylation of several other substrates was attempted as well. Trace amounts of product were observed by GC when 4-methoxytoluene was employed as substrate. No borylation was seen with 3-fluorotoluene or 2,6-lutidine.

It was hypothesized that the borylation reaction could involve exchange of halide ligands in the cobalt complex with alkoxy groups. To investigate this possibility, m-xylene was subjected to borylation using cobalt complex 3 and KOtBu as activator. In a nitrogen-filled glove box, a 3 mL Wheaton® vial was charged with cobalt complex 3 (19.8 mg, 0.025 mmol, 2.5 mol %) and KOtBu (17 mg, 0.15 mmol). THF (0.5 mL) was then added. The resulting mixture was then stirred for about 5 min. Then, m-xylene (367 µL, 3.0 mmol) and $B_2pin_2$ (254 mg, 1.0 mmol) were added. The vial was capped and taken out of the glove box. The reaction mixture was heated at 80° C. for 17 h. Analysis by GC showed 8% conversion of m-xylene based on $B_2pin_2$ with 1:2 ratio of benzylic to meta borylation products (Scheme 9). No reaction was observed with HBpin. Similar conversion was achieved with NaOtBu. Other bases such as LiOtBu, $K_2CO_3$, $K_3PO_4$, and KOAc were inefficient.

Scheme 9. Borylation of m-xylene using cobalt complex 3 and KOtBu as activator

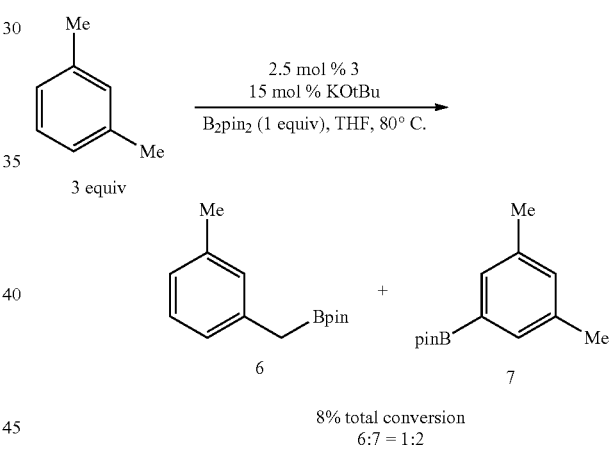

Borylation Using Cobalt Complexes Including an N-Heterocyclic Carbene (NHC)

Cobalt complexes including N-heterocyclic carbenes (NHC) as ligands were evaluated as catalysts for borylations. Using $CoCl_2$ as a cobalt source, NHC-1 as carbene precursor, and a base (KOtBu), the active cobalt catalyst could be formed in situ and successful borylation of m-xylene could be achieved (Scheme 10).

In a nitrogen-filled glove box, a 3 mL Wheaton® vial was charged with cobalt chloride (6.5 mg, 0.05 mmol, 5 mol %), 1,3-diisopropyl-1H-imidazol-3-ium chloride (18.9 mg, 0.1 mmol) and KOtBu (22.4 mg, 0.2 mmol). THF (0.5 mL) was added, and the resulting mixture was stirred for about 10 min. A purple colored solution formed. Then, m-xylene (367 µL, 3.0 mmol) and HBpin (145 µL, 3.0 mmol) were added. The vial was capped and taken out of the glove box. The reaction mixture was then heated at 80° C. for 16 h. Analysis by GC showed 40% conversion of m-xylene based on HBpin. Under the same reaction conditions, $B_2pin_2$ afforded none of the borylated product. Under the same reaction conditions, ethylbenzene gave 56% conversion of starting material (45% conversion to the benzylic borylation product).

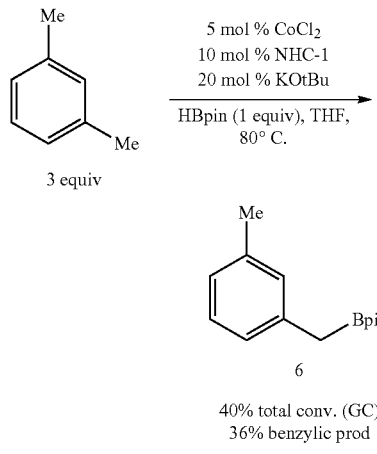

Scheme 10. Borylation of m-xylene using an in situ formed carbene-ligated cobalt complex 40% total conv. (GC)
36% benzylic prod It was hypothesized that the active borylation catalyst in the reaction above was an NHC-ligated cobalt alkoxide formed in situ during the borylation reaction. To test this hypothesis, the presumed active borylation catalyst (NHC-1) was synthesized and isolated. Briefly, CoCl₂ was reacted with NHC-1 in the presence of KOtBu base to afford cobalt catalyst 8 in 88% yield after recrystallization (Scheme 11).

An oven-dried flask was charged inside nitrogen-filled glove box with CoCl₂ (168 mg, 1.3 mmol) and 1,3-diisopropyl-1H-imidazol-3-ium chloride (490 mg, 2.6 mmol). THF (8 mL) and KOtBu (583 mg, 5.2 mmol) were then added sequentially. The resulting mixture was stirred inside glove box for 1 h. Then, the solvent was removed under vacuum, and the residue was suspended in toluene and filtered through Celite®. The filtrate was collected, and the solvent removed under vacuum providing 635 mg of dark purple crystalline material. Recrystallization from pentane at −35° C. afforded 582 mg (88%) of cobalt complex 8. Single crystal X-ray diffraction confirmed the structure. ¹H NMR (500 MHz, benzene-d₆, ppm) δ 41.70 (s, 4H) 39.00 (br s, 4H) 8.76 (br s, 18H) 2.31 (br s, 24H).

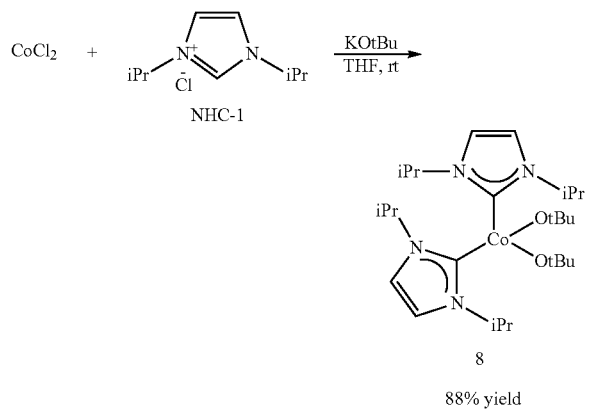

Scheme 11. Synthesis of cobalt complex 8

88% yield

Cobalt complex 8 was then evaluated as a borylation catalyst. In a nitrogen filled glove box, a 3 mL Wheaton® vial was charged with cobalt complex 8 (5.1 mg, 0.01 mmol, 2 mol %). THF (0.25 mL) and m-xylene (183 μL, 1.5 mmol) were then added sequentially. HBpin (73 μL, 0.5 mmol) was then added. The vial was capped and taken out of the glove box. The reaction mixture was then heated at 80° C. for 16 h. Analysis by GC showed 80% conversion of m-xylene based on HBpin. 62% of monoborylated product 6 was formed together with 13% of gem-diBpin product 9.

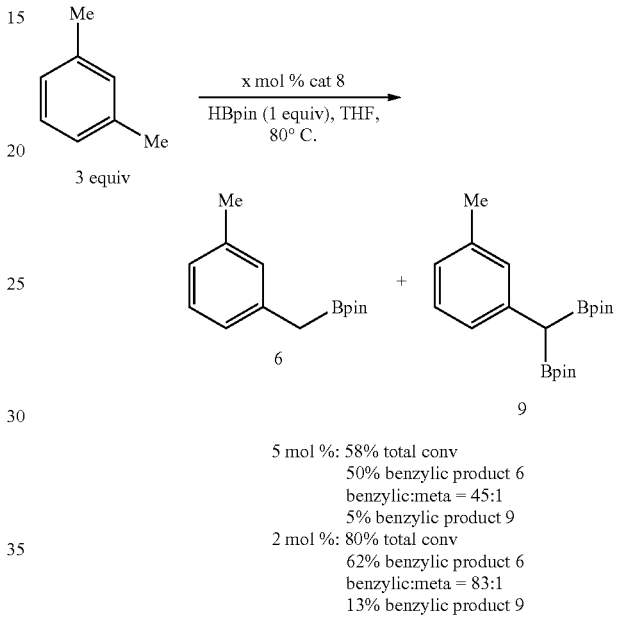

Scheme 12. Borylation of m-xylene using complex 8

5 mol %: 58% total conv
50% benzylic product 6
benzylic:meta = 45:1
5% benzylic product 9
2 mol %: 80% total conv
62% benzylic product 6
benzylic:meta = 83:1
13% benzylic product 9

In another experiment, the borylation reaction was performed using the substrate as a limiting reagent. In a nitrogen-filled glove box, a 3 mL Wheaton® vial was charged with cobalt complex 8 (10.2 mg, 0.02 mmol, 2 mol %). Next, THF (0.25 mL) and m-xylene (122 μL, 1.0 mmol) were added. Then, HBpin (290 μL, 2.0 mmol) was added. The vial was capped and taken out of the glove box. The reaction mixture was heated at 80° C. for 17 h. Analysis by GC showed 71% conversion of m-xylene: 37% of monoborylated product 6 was formed together with 29% of gem-diBpin product 9 and 5% of unidentified diBpin product.

It was also discovered that B₂pin₂ can be used as the main boron source if a catalytic amount of HBpin is added to activate cobalt precatalyst 8. In a nitrogen-filled glove box, a 3 mL Wheaton® vial was charged with cobalt complex 8 (10.2 mg, 0.02 mmol, 2 mol %). THF (0.5 mL) and m-xylene (122 μL, 1.0 mmol) were added. Then, HBpin (11.6 μL, 0.08 mmol, 8 mol %) and B₂pin₂ (381 mg, 1.5 mmol) were added. The vial was capped and taken out of the glove box. The reaction mixture was heated at 80° C. for 16 h. Analysis by GC showed 77% conversion of m-xylene: 31% of monoborylated product 6 was formed together with 40% of gem-diBpin product 9 and 6% of unidentified diBpin product. Prolonged heating up to 40 hours did not improve conversion and product ratios. Isolation of products was done by flash column chromatography on silica gel using pentane-diethyl ether mixtures as eluent. 4,4,5,5-Tetramethyl-2-(3-methylbenzyl)-1,3,2-dioxaborolane was isolated as colorless oil in 19% yield. $^1$H NMR (500 MHz, CDCl$_3$, ppm) δ 7.14 (dd, 1H, J=7.2, 7.2 Hz) 7.02-6.98 (m, 2H) 6.95 (d, 1H, J=7.5 Hz) 2.32 (s, 3H) 2.27 (s, 2H) 1.25 (s, 12H). $^{13}$C NMR (125 MHz, CDCl$_3$, ppm) δ 138.4, 137.7, 129.8, 128.1, 125.9, 125.6, 83.4, 24.7, 21.4. Signal for one carbon is not located. $^{11}$B NMR (160 MHz, CDCl$_3$, ppm) δ 33.0. 2,2'-(m-Tolylmethylene)-bis(4,4,5,5-tetramethyl-1,3,2-dioxaborolane) was isolated in 21% yield. $^1$H NMR (500 MHz, CDCl$_3$, ppm) δ 7.14-7.09 (m, 2H) 7.05 (s, 1H) 6.92-6.88 (m, 1H) 2.30 (s, 3H) 2.27 (s, 1H) 1.24 (s, 12H) 1.23 (s, 12H). $^{11}$B NMR (160 MHz, CDCl$_3$, ppm) δ 32.9.

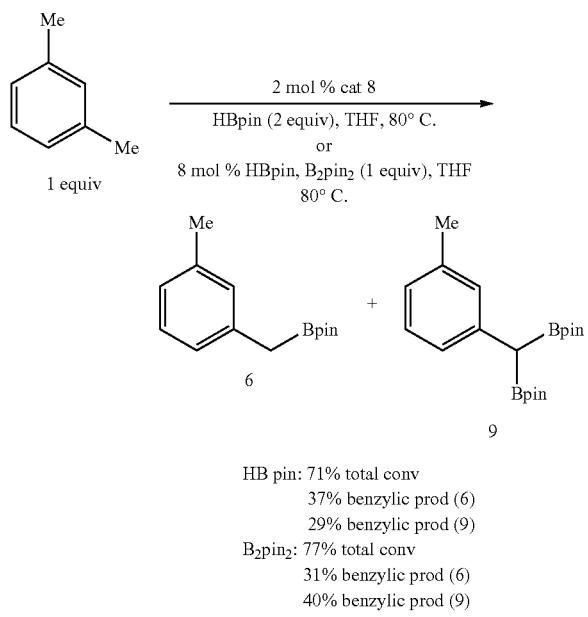

Scheme 13. Borylation of m-xylene (limiting) using complex 8 and B$_2$pin$_2$

HB pin: 71% total conv
37% benzylic prod (6)
29% benzylic prod (9)
B$_2$pin$_2$: 77% total conv
31% benzylic prod (6)
40% benzylic prod (9)

Additional substrates were also evaluated. Borylation of 4-chlorotoluene afforded the halogen-boron exchange product in trace amounts. No other borylated products were detected. 3-Fluorotoluene was defluorinated under reaction conditions. Only trace amount of a borylated material were observed in $^{11}$B-NMR. 2-Methylthiophene was unreactive under reaction conditions. In separate experiment, using equivimolar amounts of 2-methylthiophene and m-xylene, it was confirmed that thiophene could act as a catalyst poison as no borylation of m-xylene was observed. Trace borylation of 2,6-lutidine was observed by GC and GC-MS as well.

A reaction performed using 3-Methylanisole afforded a mixture of products that arise from the reduction-borylation sequence. In a nitrogen-filled glove box, a 3 mL Wheaton® vial was charged with cobalt complex 8 (10.2 mg, 0.02 mmol, 2 mol %). 0THF (0.24 mL) and 3-methylanisole (126 μL, 1.0 mmol) were then added. Then, HBpin (290 μL, 2.0 mmol) was added. The vial was capped and taken out of the glove box. The reaction mixture was heated at 80° C. for 18 h. Analysis by GC showed 11% of α-Bpin-toluene, 25% of α,α-diBpin-toluene, and 16% of toluene.

The compositions and methods of the appended claims are not limited in scope by the specific compositions and methods described herein, which are intended as illustrations of a few aspects of the claims. Any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A process for preparing a borylated aromatic compound comprising contacting an aromatic substrate with a catalytic cobalt complex and a borylation reagent under conditions effective to form the borylated aromatic compound,
   wherein the borylated aromatic compound comprises a boronic acid or a boronic acid derivative covalently bound to a carbon atom of an aromatic ring,
   wherein the catalytic cobalt complex comprises a complex defined by the formula below

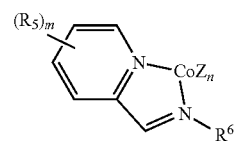

wherein
Z is, independently for each occurrence, a halide, a C$_1$-C$_6$ alkyl group, or an aryl group,
n is 2,
R$^5$ is, individually for each occurrence, a halogen, —OR$^7$, —NR$^7$R$^7$, —C(=O)R$^8$, a nitrile group, a C$_1$-C$_6$ alkyl group, an aryl group, or a C$_1$-C$_6$ haloalkyl group,
m is 0, 1, 2, 3, or 4,
R$^6$ is selected from one of the following:

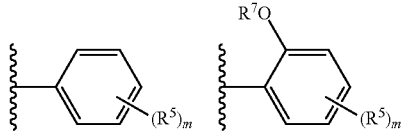

R⁷ is, individually for each occurrence, hydrogen or a C₁-C₆ alkyl group, and

R⁸ is, individually for each occurrence, hydrogen, —OR⁷, —NR⁷R⁷, or a C₁-C₆ alkyl group.

2. The process of claim 1, wherein the aromatic substrate is selected from the group consisting of a substituted or unsubstituted aryl compound, a substituted or unsubstituted six-membered heteroaromatic compound, a substituted or unsubstituted five-membered heteroaromatic compound, and combinations thereof.

3. The process of claim 1, wherein the aromatic substrate is a substituted or unsubstituted aryl compound and the substituted or unsubstituted aryl compound comprises a compound defined by Formula I Formula I wherein A is, individually for each occurrence, hydrogen, a halogen, —OR¹,
—NR²R³, —C(=O)R⁴, a nitrile group, a C₁-C₆ alkyl group, a C₁-C₆ haloalkyl group, or a boronic acid or a boronic acid derivative, R¹, R², and R³ are each, individually for each occurrence, hydrogen or a C₁-C₆ alkyl group, and R⁴ is, individually for each occurrence, hydrogen, —OR¹, —NR²R³, or a C₁-C₆ alkyl group; and wherein the borylated aromatic compound comprises a compound defined by Formula II Formula II wherein A is, for each occurrence, as described above and Y is a boronic acid or a boronic acid derivative.

4. The process of claim 3, wherein the borylated aromatic compound comprises a compound defined by Formula II wherein Y is a boronic acid derivative selected from one of the following:

5. The process of claim 1, wherein the aromatic substrate is a six-membered heteroaromatic compound and the six-membered heteroaromatic compound comprises a compound defined by one of Formula IIIa, Formula IIIb, or Formula IIIc Formula IIIa Formula IIIb Formula IIIc wherein A is, individually for each occurrence, hydrogen, a halogen, —OR¹,
—NR²R³, —C(=O)R⁴, a nitrile group, a C₁-C₆ alkyl group, a C₁-C₆ haloalkyl group, or a boronic acid or a boronic acid derivative, R¹, R², and R³ are each, individually for each occurrence, hydrogen or a C₁-C₆ alkyl group, and R⁴ is, individually for each occurrence, hydrogen, —OR¹, —NR²R³, or a C₁-C₆ alkyl group; and wherein the borylated aromatic compound comprises a compound defined by one of Formula IVa, Formula IVb, or Formula IVc Formula IVa Formula IVb Formula IVc wherein A is, for each occurrence, as described above and Y is a boronic acid or a boronic acid derivative.

6. The process of claim 5, wherein the borylated aromatic compound comprises a compound defined by one of Formula IVa, Formula IVb, or Formula IVc, wherein Y is a boronic acid derivative selected from one of the following:

7. The process of claim 1, wherein the aromatic substrate is a five-membered heteroaromatic compound and the five-membered heteroaromatic compound comprises a compound defined by one of Formula Va or Formula Vb Formula Va Formula Vb wherein X is NH, O, or S;

A is, individually for each occurrence, hydrogen, a halogen, —OR$^1$, —NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group; and wherein the borylated aromatic compound comprises a compound defined by one of Formula VIa or Formula VIb Formula VIa Formula VIb wherein A is, for each occurrence, as described above and Y is a boronic acid or a boronic acid derivative.

8. The process of claim 7, wherein the borylated aromatic compound comprises a compound defined by one of Formula VIa or Formula VIb, wherein Y is a boronic acid derivative selected from one of the following:

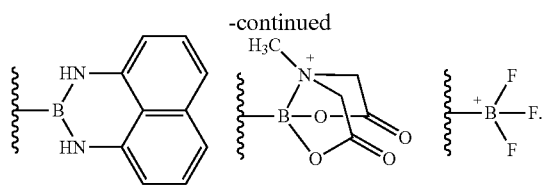

9. The process of claim 1, wherein the borylation reagent comprises a B—B bond, a B—H bond, or a combination thereof.

10. The process of claim 1, wherein the borylation reagent comprises one or more of the following:

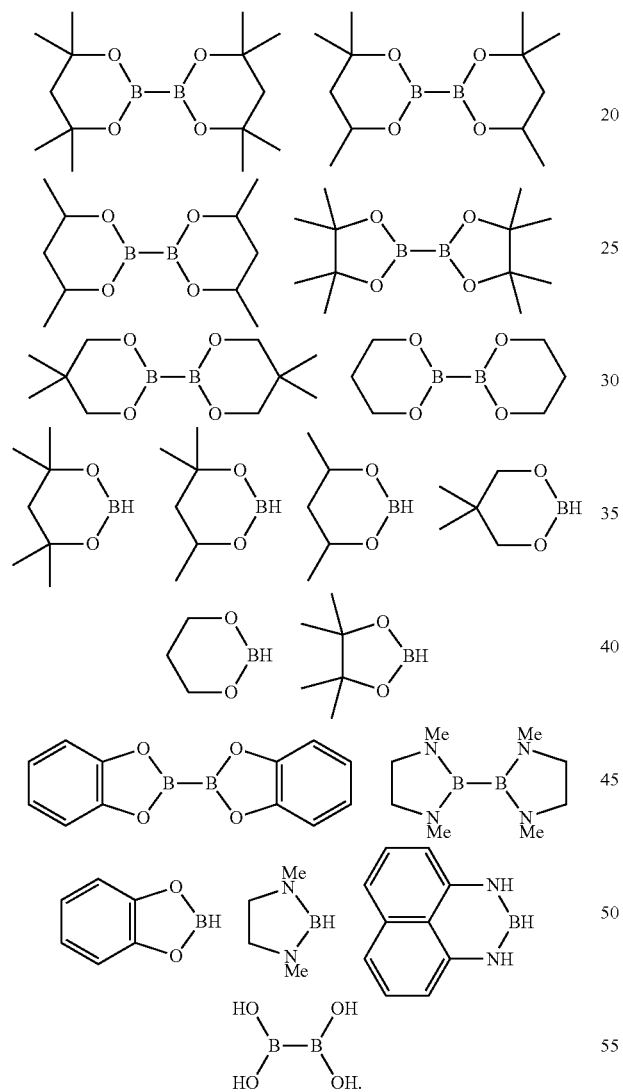

11. The process of claim 1, wherein the catalytic cobalt complex comprises a cobalt(I) complex.

12. The process of claim 1, wherein the catalytic cobalt complex comprises a cobalt chelate complex comprising a bidentate ligand.

13. The process of claim 1, wherein the aromatic substrate is contacted with the catalytic cobalt complex and the borylation reagent at a temperature of from greater than 25° C. to 85° C.

14. A process for preparing a borylated aromatic compound comprising contacting an aromatic substrate with a catalytic cobalt complex and a borylation reagent under conditions effective to form the borylated aromatic compound, wherein the borylated aromatic compound comprises a boronic acid or a boronic acid derivative covalently bound to a carbon atom of an aromatic ring, and wherein the catalytic cobalt complex comprises a cobalt (I) complex comprising exclusively monodentate ligands.

15. The process of claim 14, wherein the aromatic substrate is selected from the group consisting of a substituted or unsubstituted aryl compound, a substituted or unsubstituted six-membered heteroaromatic compound, a substituted or unsubstituted five-membered heteroaromatic compound, and combinations thereof.

16. The process of claim 14, wherein the aromatic substrate is a substituted or unsubstituted aryl compound and the substituted or unsubstituted aryl compound comprises a compound defined by Formula I

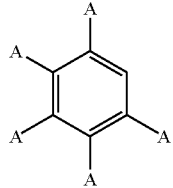

Formula I wherein

A is, individually for each occurrence, hydrogen, a halogen, —OR$^1$,

—NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group; and wherein the borylated aromatic compound comprises a compound defined by Formula II

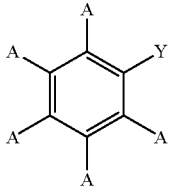

Formula II wherein A is, for each occurrence, as described above and Y is a boronic acid or a boronic acid derivative.

17. The process of claim 16, wherein the borylated aromatic compound comprises a compound defined by Formula II wherein Y is a boronic acid derivative selected from one of the following:

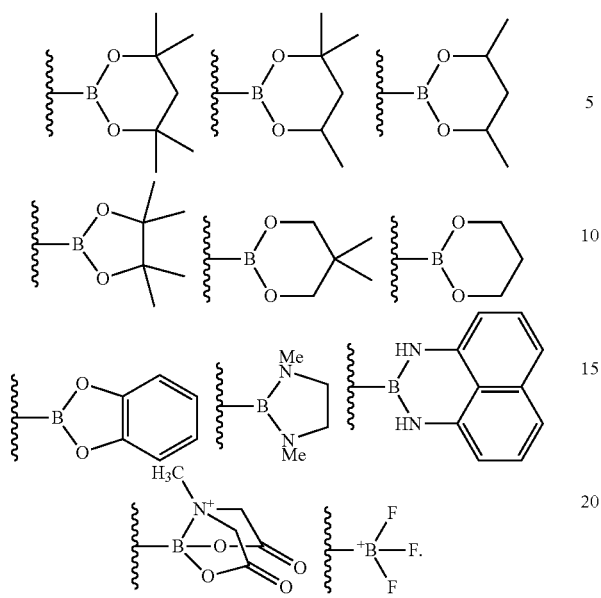

18. The process of claim 14, wherein the aromatic substrate is a six-membered heteroaromatic compound and the six-membered heteroaromatic compound comprises a compound defined by one of Formula IIIa, Formula IIIb, or Formula IIIc

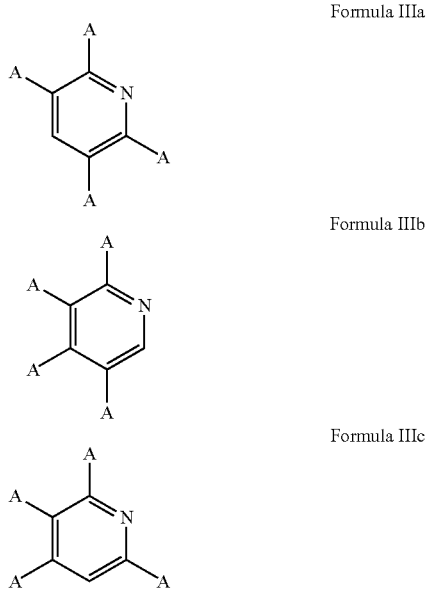

wherein
A is, individually for each occurrence, hydrogen, a halogen, —OR$^1$,
—NR$^2$R$^3$, —C(=O)R$^4$, a nitrile group, a C$_1$-C$_6$ alkyl group, a C$_1$-C$_6$ haloalkyl group, or a boronic acid or a boronic acid derivative,
R$^1$, R$^2$, and R$^3$ are each, individually for each occurrence, hydrogen or a C$_1$-C$_6$ alkyl group, and
R$^4$ is, individually for each occurrence, hydrogen, —OR$^1$, —NR$^2$R$^3$, or a C$_1$-C$_6$ alkyl group; and wherein the borylated aromatic compound comprises a compound defined by one of Formula IVa, Formula IVb, or Formula IVc

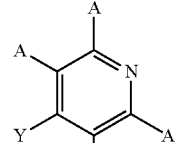
Formula IVa

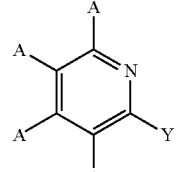
Formula IVb

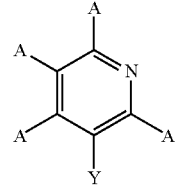
Formula IVc wherein A is, for each occurrence, as described above and Y is a boronic acid or a boronic acid derivative.

19. The process of claim 18, wherein the borylated aromatic compound comprises a compound defined by one of Formula IVa, Formula IVb, or Formula IVc, wherein Y is a boronic acid derivative selected from one of the following:

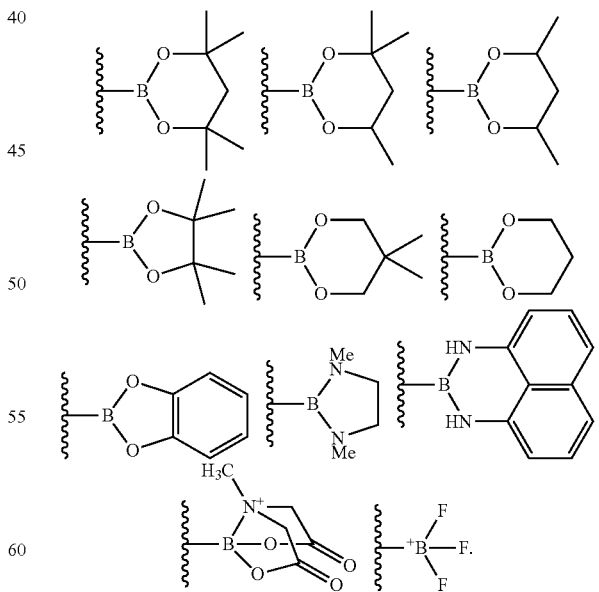

20. The process of claim 14, wherein the aromatic substrate is a five-membered heteroaromatic compound and the five-membered heteroaromatic compound comprises a compound defined by one of Formula Va or Formula Vb

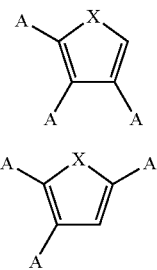

Formula Va

Formula Vb

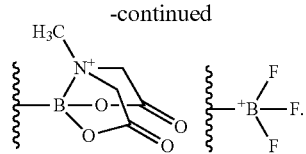

22. The process of claim 14, wherein the borylation reagent comprises a B—B bond, a B—H bond, or a combination thereof.

23. The process of claim 14, wherein the borylation reagent comprises one or more of the following:

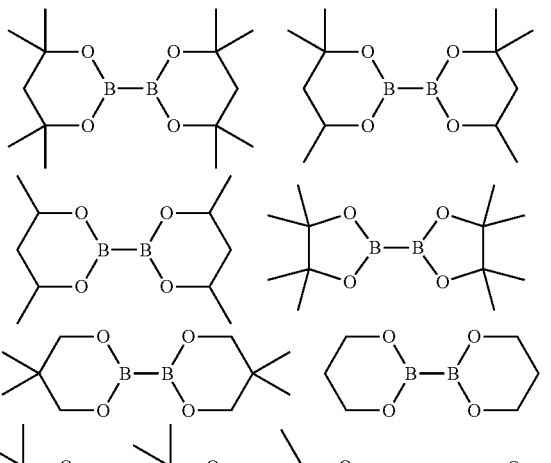

wherein
X is NH, O, or S;
A is, individually for each occurrence, hydrogen, a halogen, —OR$^1$,
—NR$^2$R$^3$, —C(=O)R$^4$, a nitrile group, a C$_1$-C$_6$ alkyl group, a C$_1$-C$_6$ haloalkyl group, or a boronic acid or a boronic acid derivative,
R$^1$, R$^2$, and R$^3$ are each, individually for each occurrence, hydrogen or a C$_1$-C$_6$ alkyl group, and
R$^4$ is, individually for each occurrence, hydrogen, —OR$^1$, —NR$^2$R$^3$, or a C$_1$-C$_6$ alkyl group; and
wherein the borylated aromatic compound comprises a compound defined by one of Formula VIa or Formula VIb

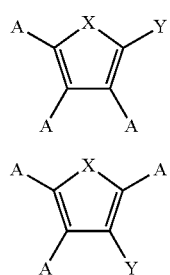

Formula VIa

Formula VIb wherein A is, for each occurrence, as described above and Y is a boronic acid or a boronic acid derivative.

21. The process of claim 20, wherein the borylated aromatic compound comprises a compound defined by one of Formula VIa or Formula VIb, wherein Y is a boronic acid derivative selected from one of the following:

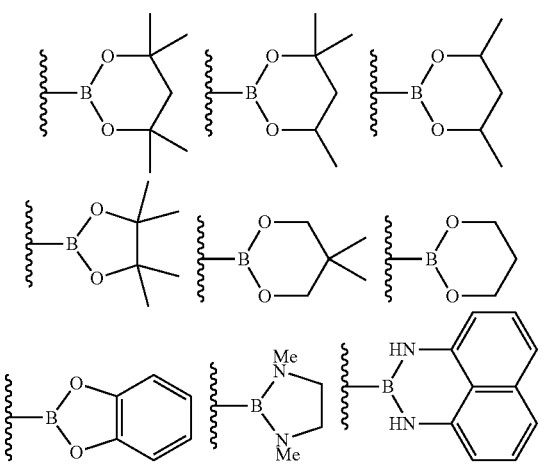

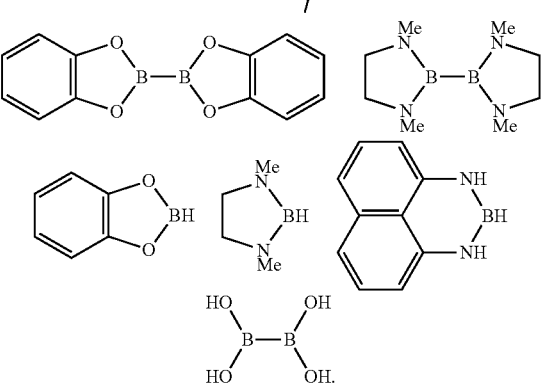

24. The process of claim 14, wherein the catalytic cobalt complex comprises Py$_2$Co(CH$_2$SiMe$_3$)$_2$.

25. The process of claim 14, wherein the aromatic substrate is contacted with the catalytic cobalt complex and the borylation reagent at a temperature of from greater than 25° C. to 85° C.

26. A process for preparing a borylated aromatic compound comprising contacting an aromatic substrate with a catalytic cobalt complex and a borylation reagent under conditions effective to form the borylated aromatic compound, wherein the borylated aromatic compound comprises a boronic acid or a boronic acid derivative covalently bound to a carbon atom of an aromatic ring, and wherein the catalytic cobalt complex comprises a bridged dicobalt complex.

27. The process of claim 26, wherein the aromatic substrate is selected from the group consisting of a substituted or unsubstituted aryl compound, a substituted or unsubstituted six-membered heteroaromatic compound, a substituted or unsubstituted five-membered heteroaromatic compound, and combinations thereof.

28. The process of claim 26, wherein the aromatic substrate is a substituted or unsubstituted aryl compound and the substituted or unsubstituted aryl compound comprises a compound defined by Formula I

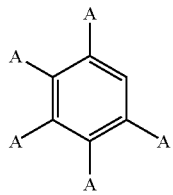

Formula I wherein
A is, individually for each occurrence, hydrogen, a halogen, —OR$^1$,
—NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group; and wherein the borylated aromatic compound comprises a compound defined by Formula II

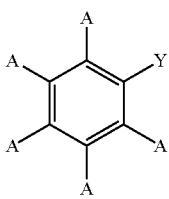

Formula II wherein A is, for each occurrence, as described above and Y is a boronic acid or a boronic acid derivative.

29. The process of claim 28, wherein the borylated aromatic compound comprises a compound defined by Formula II wherein Y is a boronic acid derivative selected from one of the following:

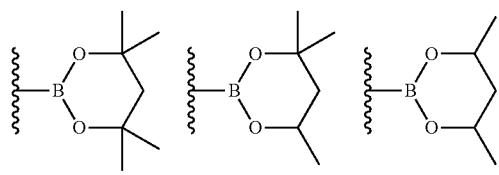

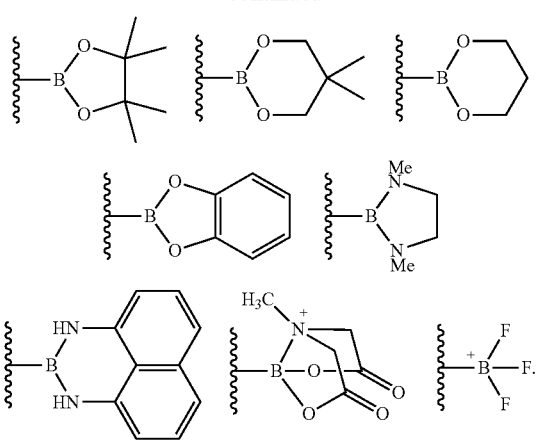

30. The process of claim 26, wherein the aromatic substrate is a six-membered heteroaromatic compound and the six-membered heteroaromatic compound comprises a compound defined by one of Formula IIIa, Formula IIIb, or Formula IIIc

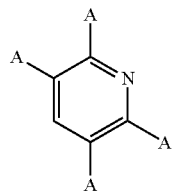

Formula IIIa

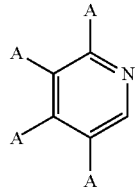

Formula IIIb

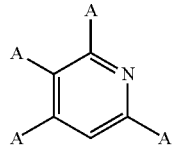

Formula IIIc wherein
A is, individually for each occurrence, hydrogen, a halogen, —OR$^1$,
—NR$^2$R$^3$, —C(=O)R$^4$, a nitrile group, a C$_1$-C$_6$ alkyl group, a C$_1$-C$_6$ haloalkyl group, or a boronic acid or a boronic acid derivative, R$^1$, R$^2$, and R$^3$ are each, individually for each occurrence, hydrogen or a C$_1$-C$_6$ alkyl group, and R$^4$ is, individually for each occurrence, hydrogen, —OR$^1$, —NR$^2$R$^3$, or a C$_1$-C$_6$ alkyl group; and wherein the borylated aromatic compound comprises a compound defined by one of Formula IVa, Formula IVb, or Formula IVc

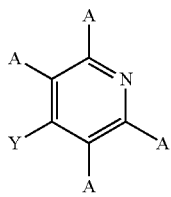

Formula IVa

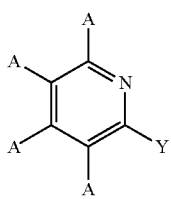

Formula IVb

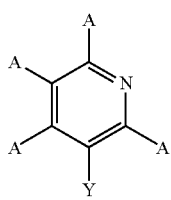

Formula IVc wherein A is, for each occurrence, as described above and Y is a boronic acid or a boronic acid derivative.

31. The process of claim 30, wherein the borylated aromatic compound comprises a compound defined by one of Formula IVa, Formula IVb, or Formula IVc, wherein Y is a boronic acid derivative selected from one of the following:

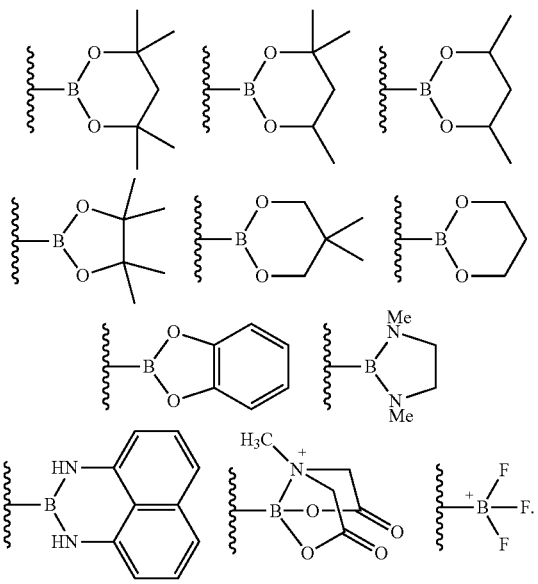

32. The process of claim 26, wherein the aromatic substrate is a five-membered heteroaromatic compound and the five-membered heteroaromatic compound comprises a compound defined by one of Formula Va or Formula Vb

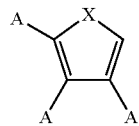

Formula Va

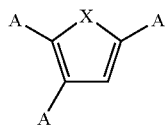

Formula Vb wherein
X is NH, O, or S;
A is, individually for each occurrence, hydrogen, a halogen, —OR$^1$, —NR$^2$R$^3$, —C(=O)R$^4$, a nitrile group, a C$_1$-C$_6$ alkyl group, a C$_1$-C$_6$ haloalkyl group, or a boronic acid or a boronic acid derivative,
R$^1$, R$^2$, and R$^3$ are each, individually for each occurrence, hydrogen or a C$_1$-C$_6$ alkyl group, and
R$^4$ is, individually for each occurrence, hydrogen, —OR$^1$, —NR$^2$R$^3$, or a C$_1$-C$_6$ alkyl group; and
wherein the borylated aromatic compound comprises a compound defined by one of Formula VIa or Formula VIb

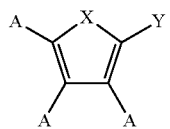

Formula VIa

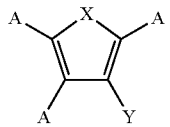

Formula VIb wherein A is, for each occurrence, as described above and Y is a boronic acid or a boronic acid derivative.

33. The process of claim 32, wherein the borylated aromatic compound comprises a compound defined by one of Formula VIa or Formula VIb, wherein Y is a boronic acid derivative selected from one of the following:

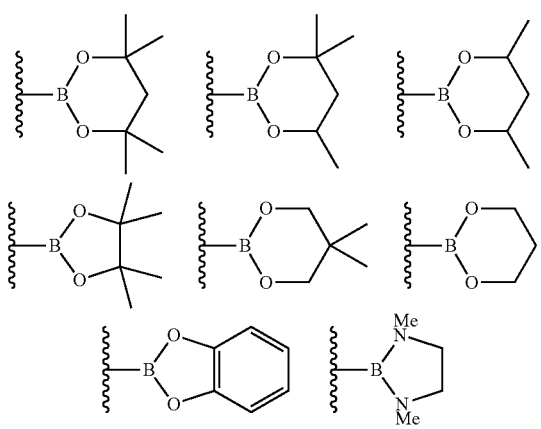

-continued

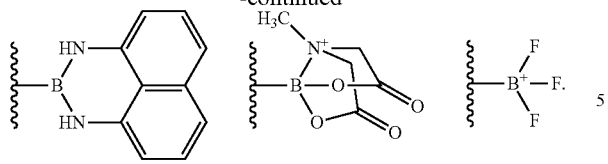

34. The process of claim 26, wherein the borylation reagent comprises a B—B bond, a B—H bond, or a combination thereof.

35. The process of claim 26, wherein the borylation reagent comprises one or more of the following:

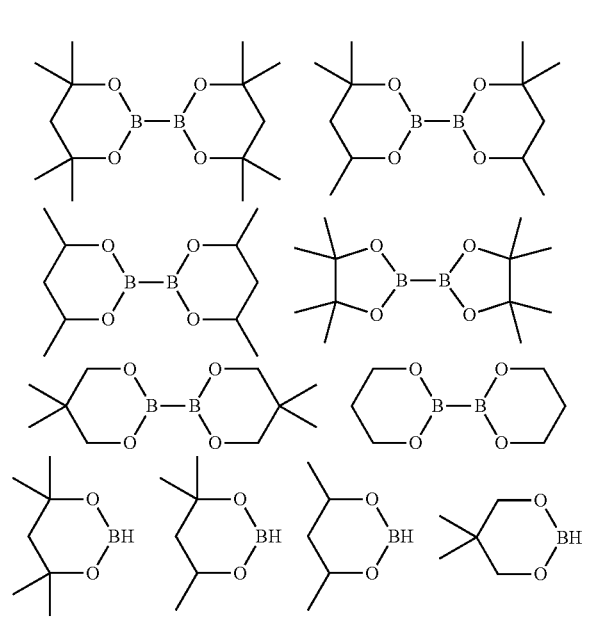

-continued

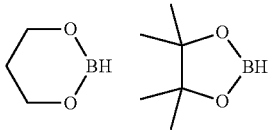

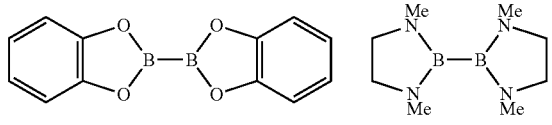

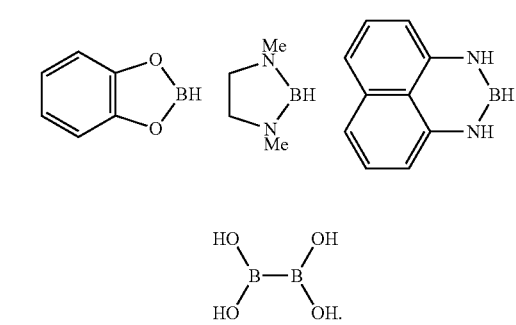

36. The process of claim 26, wherein the catalytic cobalt complex comprises [(Cp*Co)$_2$-μ-(η$^4$:η$^4$-toluene)].

37. The process of claim 26, wherein the aromatic substrate is contacted with the catalytic cobalt complex and the borylation reagent at a temperature of from greater than 25° C. to 85° C.

* * * * *

UNITED STATES PATENT AND TRADEMARK OFFICE
CERTIFICATE OF CORRECTION

PATENT NO. : 10,166,533 B2
APPLICATION NO. : 14/740814
DATED : January 1, 2019
INVENTOR(S) : Milton R. Smith et al.

Page 1 of 1

It is certified that error appears in the above-identified patent and that said Letters Patent is hereby corrected as shown below:

On the Title Page

Please replace the Assignee names with the following:
Assignees: Dow AgroSciences LLC, Indianapolis, IN (US); Board of Trustees of Michigan State University, East Lansing, MI (US)

Signed and Sealed this
Eleventh Day of February, 2020

Andrei Iancu
*Director of the United States Patent and Trademark Office*